(12) United States Patent
Pastan et al.

(10) Patent No.: US 7,081,518 B1
(45) Date of Patent: Jul. 25, 2006

(54) ANTI-MESOTHELIN ANTIBODIES HAVING HIGH BINDING AFFINITY

(75) Inventors: Ira Pastan, Potomac, MD (US); Partha S. Chowdhury, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/979,539

(22) PCT Filed: May 26, 2000

(86) PCT No.: PCT/US00/14829

§ 371 (c)(1),
(2), (4) Date: Nov. 20, 2001

(87) PCT Pub. No.: WO00/73346

PCT Pub. Date: Dec. 7, 2000

Related U.S. Application Data

(60) Provisional application No. 60/160,071, filed on May 27, 1999.

(51) Int. Cl.
| | |
|---|---|
| C12P 21/08 | (2006.01) |
| A61K 39/395 | (2006.01) |
| C07H 21/04 | (2006.01) |
| C12P 21/04 | (2006.01) |
| C12Q 1/70 | (2006.01) |
| C12N 7/00 | (2006.01) |
| C12N 15/70 | (2006.01) |

(52) U.S. Cl. .............. 530/387.3; 530/388.1; 530/388.8; 530/391.7; 424/133.1; 424/135.1; 424/155.1; 424/181.1; 435/69.6; 536/23.53

(58) Field of Classification Search ............ 530/387.1, 530/387.3, 387.7, 388.8, 388.1, 391.7; 435/5, 435/69.6; 424/130.1, 133.1, 134.1, 135.1, 424/138.1, 181.1, 183.1, 155.1; 536/23.53
See application file for complete search history.

(56) References Cited

U.S. PATENT DOCUMENTS

| | | | |
|---|---|---|---|
| 5,320,956 A | | 6/1994 | Willingham et al. |
| 5,498,698 A | | 3/1996 | Yamaguchi et al. |
| 5,530,101 A | * | 6/1996 | Queen et al. |
| 5,723,318 A | | 3/1998 | Yamaguchi et al. |
| 5,747,654 A | | 5/1998 | Pastan et al. |
| 5,977,322 A | * | 11/1999 | Marks et al. |
| 6,083,502 A | * | 7/2000 | Pastan et al. |
| 6,153,430 A | | 11/2000 | Pastan et al. |
| 6,809,184 B1 | | 10/2004 | Pastan et al. |

FOREIGN PATENT DOCUMENTS

| | | |
|---|---|---|
| WO | WO 92/07081 A2 | 4/1992 |
| WO | WO 97/25068 A2 | 7/1997 |
| WO | WO 97/34634 A1 | 9/1997 |

OTHER PUBLICATIONS

Rudikoff et al. Proc. Natl. Acad. Sci. USA 1982 vol. 79, pp. 1979-1983.*
William E. Paul M.D. ed. Fundamenta immunology. 3rd ed. 1993, p. 242.*
Yelton et al. The Journal of Immunology. 155: 1994-2004, 1995.*
Goyenechea et al. Proc. Natl. Acad. Sci. USA. 93:13979-13984,1996.*
Wagner et al. Nature 376: 732, Aug. 31, 1995.*
Chowdhury et al. Proc. Natl. Acad. Sci. USA 95: 669-674, Jan. 1998.*
Dhowdhury et al. Journal of Molecular Biology. 281: 917-928, 1998.*
Schier et al. Journal of Molecular Biology, 263:551-567, 1996.*
Brinkman, U. et al., "Cloning and Expression of the Roconbinant FAb Fragment of Monoclonal Antibody K1 that Reacts with Mesothelin Present on Mesotheliomas and Ovarian Cancers," *International Journal of Cancer*, May 16, 1997, vol. 71, No. 4, pp. 638-644.
Chang, K., et al., "Molecular cloning of mesothelin, a differentiation antigen present on mesothelium, mesotheliomas, and ovarian cancers," *Proc. Natl. Acad. Sci. USA*, Jan. 1996, vol. 93, pp. 136-140.

(Continued)

*Primary Examiner*—Larry R. Helms
*Assistant Examiner*—David J. Blanchard
(74) *Attorney, Agent, or Firm*—Townsend and Townsend and Crew LLP

(57) ABSTRACT

Mesothelin is a differentiation antigen present on the surface of ovarian cancers, mesotheliomas and several other types of human cancers. Because among normal tissues, mesothelin is only present on mesothelial cells, it represents a good target for antibody mediated delivery of cytotoxic agents. The present invention is directed to anti-mesothelin antibodies, including Fv molecules with particularly high affinity for mesothelin, and immunoconjugates employing them. Also described are diagnostic and therapeutic methods using the antibodies. The anti-mesothelin antibodies are well-suited for the diagnosis and treatment of cancers of the ovary, stomach, squamous cells, mesotheliomas and other malignant cells expressing mesothelin.

17 Claims, 4 Drawing Sheets

OTHER PUBLICATIONS

Chang, K., et al., "Characterization of the Antigen (CAK1) Recognized by Monoclonal Antibody K1 Present on Ovarian Cancers and Normal Mesothelium," *Cancer Research*, Jan. 1, 1992, vol. 52, No. 1, pp. 181-186.

Chowdhury, P., et al., "Isolation of Anti-Mesothelin Antibodies From A Phage Display Library," *Molecular Immunology*, Jan. 1997, vol. 34, No. 1, pp. 9-20.

Chowdhury, P., et al., "Improving antibody affinity by mimicking somatic hypermutation In vitro," *Nature Biotechnology*, Jun. 1999, vol. 17, pp. 568-572.

Colman, P.M., "Effects of amino acid sequence changes on antibody-antigen interactions," *Research in Immunology*, 1994, vol. 145, pp. 33-36.

Davies, J. et al., "Affinity improvement of single antibody VH domains: Residues in all three hypervariable regions affect antigen binding," *Immunotechnology*, 1996, vol. 2, No. 3, pp. 169-179.

Dorner, T., et al., "Delineation of Selective Influences Shaping the Mutated Expressed Human Ig Heavy Chain Repertoire, " *J. Immunol.*, 1998, vol. 160, No. 6, pp. 2831-2841.

Green, N., et al., "Somatic hypermutation of antibody genes: a hot spot warms up," *BioEssaays*, Mar. 1998, vol. 20, No. 3, pp. 227-234.

Heidelberg, Database EMBL (EMPRO) EMBL, Mar. 10, 1998.

Kuby, J., W.H., "Chapter 6: Antigen-Antibody Interactions," *Immunology, Second Edition*, Freeman and Company, New York, USA, 1994, pp. 136-134.

Wu, G., et al., "Stepwise in vitro affinity maturation of Vitaxin, an $\alpha_v\beta_3$-specific humanized mAb," *Proc. Natl. Acad. Sci. US*, May 1998, vol. 95, pp. 6037-6042.

Yamaguchi, N., et al., "A Novel Cytokine Exhibiting Megakaryocyte Potentiating Activity form a Human Pancreatic Tumor Cell Line HPC-Y5," *The Journal of Biological Chemistry*, 1994, pp. 805-808.

* cited by examiner

| CLONE | RESIDUES RANDOMIZED | CLONE NAME | 89 cag Q | 90 cag Q | 91 tgg W | 92 agt S | 93 ggt G | 94 tac Y | 95 cct P | 96 ctc L | 97 acg T |
|---|---|---|---|---|---|---|---|---|---|---|---|
| PARENTAL | NONE | SS | Q | | | | | | | | |
| LIB 89/93/94 | 89, 93 AND 94 | SS1 | Q | | | | → K | → H | | | |
| | | C5* | Q | | | | G | H | | | |
| | | D7* | Q | | | | A | H | | | |
| | | B7 | Q | | | | Q | I | | | |
| LIB 89-91 | 89-91 | B4 | Q | Q | W | | | | | | |
| LIB 92-94 | 92-94 | D8* | | | | G | F | N | | | |
| | | D9* | | | | G | T | N | | | |
| | | C10* | | | | G | S | H | | | |
| | | C3 | | | | G | D | F | | | |
| | | C4* | | | | G | D | H | | | |
| | | E9* | | | | S | K | H | | | |
| | | E2 | | | | S | A | H | | | |
| LIB 95-97 | 95-97 | E4* | | | | | | | P | T | T |

FIG. 3.

VL CDR3 NUCLEOTIDE AND AMINO ACID SEQUENCE

SEQUENCE LISTING

```
<160> NUMBER OF SEQ ID NOS: 12

<210> SEQ ID NO 1
<211> LENGTH: 241
<212> TYPE: PRT
<213> ORGANISM: Artificial Sequence
<220> FEATURE:
<223> OTHER INFORMATION: Description of Artificial Sequence:SS single
      chain Fv antibody (SS scFv)

<400> SEQUENCE: 1

Met Gln Val Gln Leu Gln Gln Ser Gly Pro Glu Leu Glu Lys Pro Gly
  1               5                  10                  15

Ala Ser Val Lys Leu Ser Cys Lys Ala Ser Gly Tyr Ser Phe Thr Gly
             20                  25                  30

Tyr Thr Met Asn Trp Val Lys Gln Ser His Gly Lys Ser Leu Glu Trp
         35                  40                  45

Ile Gly Leu Ile Thr Pro Tyr Asn Gly Ala Ser Ser Tyr Asn Gln Lys
     50                  55                  60

Phe Arg Gly Lys Ala Thr Leu Thr Val Asp Lys Ser Ser Ser Thr Ala
 65                  70                  75                  80

Tyr Met Asp Leu Leu Ser Leu Thr Ser Glu Asp Ser Ala Val Tyr Phe
                 85                  90                  95

Cys Ala Arg Gly Gly Tyr Asp Gly Arg Gly Phe Asp Tyr Trp Gly Gln
            100                 105                 110

Gly Thr Thr Val Thr Val Ser Ser Gly Val Gly Gly Ser Gly Gly Gly
        115                 120                 125
```

```
Gly Ser Gly Gly Gly Ser Asp Ile Glu Leu Thr Gln Ser Pro Ala
    130             135                 140
Ile Met Ser Ala Ser Pro Gly Glu Lys Val Thr Met Thr Cys Ser Ala
145             150                 155                 160
Ser Ser Ser Val Ser Tyr Met His Trp Tyr Gln Gln Lys Ser Gly Thr
                165             170                 175
Ser Pro Lys Arg Trp Ile Tyr Asp Thr Ser Lys Leu Ala Ser Gly Val
        180             185                 190
Pro Gly Arg Phe Ser Gly Ser Gly Ser Gly Asn Ser Tyr Ser Leu Thr
            195             200             205
Ile Ser Ser Val Glu Ala Glu Asp Ala Thr Tyr Tyr Cys Gln Gln
    210             215             220
Trp Ser Gly Tyr Pro Leu Thr Phe Gly Ala Gly Thr Lys Leu Glu Ile
225             230             235                 240
Lys
```

```
<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence:linker
      peptide

<400> SEQUENCE: 2

Gly Val Gly Gly Ser Gly Gly Gly Gly Ser Gly Gly Gly Gly Ser
 1               5                  10                  15

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:nucleotide
      sequence encoding amino acids in CDR3 of the
      variable light chain (V-L) of SS scFv

<400> SEQUENCE: 3
cagcagtgga gtggttaccc tctcacg                                          27

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence:amino acid
      sequence of CDR3 of the variable light chain (V-L)
      of SS scFv

<400> SEQUENCE: 4

Gln Gln Trp Ser Gly Tyr Pro Leu Thr
 1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:peptide
      linker

<400> SEQUENCE: 5

Gly Gly Gly Ser
 1
```

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence:sequence
      addition at carboxyl terminus to maintain ability
      to translocate into the cytosol

<400> SEQUENCE: 6

Lys Asp Glu Leu
 1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:sequence
      addition at carboxyl terminus to maintain ability
      to translocate into the cytosol

<400> SEQUENCE: 7

Arg Glu Asp Leu
 1

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence:PE38
      C-terminal native sequence residues 609-613

<400> SEQUENCE: 8

Arg Glu Asp Leu Lys
 1               5

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence:degenerate
      oligo SS VL 89/93/94
<221> NAME/KEY: modified_base
<222> LOCATION: (1)..(50)
<223> OTHER INFORMATION: n = g, a, c or t

<400> SEQUENCE: 9
gcaccgaacg tgagaggsnn snnactccac tgsnngcagt aataagttgc         50

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence:degenerate
      oligo SS VL Mut 92-94
<221> NAME/KEY: modified_base
<222> LOCATION: (1)..(46)
<223> OTHER INFORMATION: n = g, a, c or t

<400> SEQUENCE: 10
gcaccgaacg tgagaggsnn snnsnnccac tgctggcagt aataag             46

<210> SEQ ID NO 11

-continued

```
<211> LENGTH: 50
<212> TYPE: DNA
<213> ORGANISM: Artificial Sequence
<220> FEATURE:
<223> OTHER INFORMATION: Description of Artificial Sequence:degenerate
      oligo SS VL Mut 89-91
<221> NAME/KEY: modified_base
<222> LOCATION: (1)..(50)
<223> OTHER INFORMATION: n = g, a, c or t

<400> SEQUENCE: 11
gcaccgaacg tgagagggta accactsnns nnsnngcagt aataagttgc          50

<210> SEQ ID NO 12
<211> LENGTH: 47
<212> TYPE: DNA
<213> ORGANISM: Artificial Sequence
<220> FEATURE:
<223> OTHER INFORMATION: Description of Artificial Sequence:degenerate
      oligo SS VL Mut 95-97
<221> NAME/KEY: modified_base
<222> LOCATION: (1)..(47)
<223> OTHER INFORMATION: n = g, a, c or t

<400> SEQUENCE: 12
ctttgtccca gcaccgaasn nsnnsnngta accactccac tgctgcg             47
```

ANTI-MESOTHELIN ANTIBODIES HAVING HIGH BINDING AFFINITY

CROSS-REFERENCES TO RELATED APPLICATIONS

This application is a national phase application under 35 U.S.C. § 371 of PCT/US00/14829, filed May 26, 2000, which claims the benefit of U.S. Provisional application Ser. No. 60/160,071, filed May 27, 1999.

STATEMENT AS TO RIGHTS TO INVENTIONS MADE UNDER FEDERALLY SPONSORED RESEARCH AND DEVELOPMENT

Not applicable.

BACKGROUND OF THE INVENTION

In many types of cancer cells, differentiation antigens are expressed. These antigens have been used as targets in cancer therapy. For example, CD19, CD20, CD22 and CD25 have successfully been used as targets in hematopoietic malignancies (Press, et al., *New Eng. J. Med.* 329:1219–1224 (1993); and Osterborg, et al., *J. Clin. Oncol.* 15:1567–1574 (1997)). This targeted cancer therapy has not, however, been successful with solid tumors, in large part because the targeted antigens are also expressed in tissues from which the tumors arose. Thus, such targeted therapies kill healthy cells as well as the malignant cells.

In the United States, despite therapy, an estimated 15,000 women die of ovarian cancer each year. Although less common than ovarian cancer, mesotheliomas are known to be resistant to all chemotherapeutic agents and therefore have a high mortality rate. Because of the morbidity of these cancers, new therapeutic approaches to these malignancies are needed.

Common to ovarian, squamous cell and some stomach cancers as well as mesotheliomas is the expression of mesothelin on the cell surface (Chang, et al., *Cancer Res.* 52:181–186 (1992); Chang, et al., *J. Surgical Pathology* 16:259–268 (1992); and Chang, et al., *Nat'l Acad. Sci. USA* 93:136–140 (1996)). Mesothelin is a 40 kD GPI-linked glycoprotein antigen present on the surface of mesothelial cells. It is synthesized as a 69 kD precursor which is then proteolytically processed. The 30 kD amino terminus is secreted and has been termed megakaryocyte potentiating factor (Yamaguchi, et al., *J. Biol. Chem.* 269:805–808 (1994)). The 40 kD carboxyl terminus remains bound to the membrane as mature mesothelin (Chang, et al., *Nat'l Acad. Sci. USA* 93:136–140 (1996)). Unlike many cell surface antigens present on cancer cells, the membrane-bound form of mesothelin cannot be detected in the blood of cancer patients and is not shed by cultured cells into medium (Chang, et al., *Cancer Res.* 52:181–186 (1992)). In addition to malignant cells, mesothelin is also found on the cell surface of cells of mesothelial origin, including ovarian cancers. Because damage to cells in these tissues would not lead to life-threatening consequences, the presence of mesothelin on the surface of cancer cells makes it a promising candidate for targeted therapies.

Immunotoxins are antibodies directed against cell surface antigens joined to a toxic moiety. In the treatment of cancer, the antibody preferably is directed against a cell surface antigen expressed only on cancer cells. However, if the death of normal cells which also express the surface antigen is not more life-threatening than the existence of the malignancy, antibodies directed against cell surface antigens expressed on non-malignant cells can be used in cancer therapy. The toxic moiety of the immunotoxin can be any toxin that is not harmful to non-targeted cells at low concentrations after systemic administration. Such a toxin is the *Pseudomonas aeruginosa* exotoxin (PE). Previous studies with PE have demonstrated that the active portion of the protein is composed of domain II and III, both of which are located at the carboxyl end of the toxin. Other toxins under development or consideration for use as the toxic moiety of immunotoxins are diphtheria toxin (Watson et al., *Intl J Cancer*, 61:233–40 (1995)), saporin (e.g., Chandler et al., *Intl J. Cancer* 78(1):106–11 (1998)) pokeweed antiviral protein (e.g., Ek et al., *Clin Cancer Res*, 4(7):1641–7 (1998), ricin (e.g., Ohtomo et al., *Anticancer Res*, 18(6A):4311–5 (1998)), and bryodin 1 (e.g., Francisco et al., *J Biol Chem*, 272(39):24165–9 (1997)). For use as immunotoxins, often the natural toxin molecule is altered to avoid non-specific toxicity or other undesirable effects. For example, the A and B chains of ricin are usually separated so that the toxic effect of the A chain can be used while avoiding the non-specific binding which would otherwise be provided by the B chain.

The antibodies that target the immunotoxin can be polyclonal, monoclonal, or recombinant antibodies, such as chimeras or variable region fragments. If the antibody is non-recombinant, the immunotoxin must be formed by chemical conjugation of the antibody to the toxic moiety. If the antibody is produced recombinantly, the antibody can be joined to the toxin through chemical bonding or through recombinant fusion. In recombinant fusion, cDNA encoding the antibody is inserted, in frame, into a plasmid that already contains cDNA which encodes the toxin. Of course, the reverse could be done as well; the toxin cDNA can be inserted into a plasmid carrying cDNA which encodes the antibody.

Because of the potential large size of the immunotoxin, it is sometimes desired to join only a fragment of an antibody to the toxic moiety. Fab, Fab' and F(ab)$_2$ fragments can be made from polyclonal, monoclonal and chimeric antibodies and then joined to the toxin through chemical bonding.

Alternatively, a cDNA can be produced in which the variable regions of an antibody are connected to essential framework regions. These smaller antibodies are then secreted as double chain Fv antibodies or, if the heavy and light chain regions are joined either directly or through a peptide linker, as single chain Fv antibodies (scFv).

One method of creating a scFv is through phage display libraries made from splenic mRNA of mice immunized with an immunogen (Chowdhury, et al., *Mol. Immunol.* 34:9–20 (1997)). If a protein immunogen is naturally found in mammals but is recombinantly expressed in prokaryotes, however, the protein will not have the correct glycosylation pattern and may not have the correct conformation. Antibodies developed by the mouse in response to this immunogen may not recognize the protein in its native state. One solution to this problem is to immunize animals with the native protein made in mammalian cells, but purification from mammalian cells of sufficient amounts of some proteins, in particular cell surface proteins, may not be possible. Another solution, although not as common, is to immunize animals with cDNA which encodes the immunogen. The cDNA, under the control of an appropriate promoter, is introduced into the animal. After boosting injections and when the antibody titer reaches a maximum, the animals are sacrificed and the spleens removed to create the phage display library.

Development of targeted therapies against mesothelin-expressing malignancies has been hampered by difficulties in developing high-affinity antibodies that are internalized well. As we noted in a recent publication, Chowdhury et al., Proc Natl Acad Sci USA, 95:669–674(1998) (hereafter, "Chowdhury 1998"), purification of sufficient amounts of mesothelin from mammalian cells has not been possible, and recombinant mesothelin expressed in Escherica coli has a low affinity for mesothelin-positive cells. We there reported that, by immunizing mice with plasmids containing DNA encoding mesothelin, we were able to elicit high titers of anti-mesothelin antibodies. We further reported that, using splenic RNA and phage display technology, we were able to isolate a single-chain Fv ("scFv"), which we called SS scFv, that binds with high affinity to mesothelin.

While SS appears to be a useful targeting agent for immunoconjugates, such as immunotoxins, even higher affinity antibodies are expected to improve the ability to detect mesothelin-expressing cancers, and to enhance the ability of immunotoxins to kill cancer cells expressing mesothelin. Accordingly, a need remains for improved means of generating antibodies with high affinity to target antigens. In particular, a need remains for higher affinity antibodies to mesothelin.

SUMMARY OF THE INVENTION

The present invention relates to polypeptides which comprise a mutated antibody heavy chain variable region or a mutated antibody light chain variable region, or both, wherein the polypeptide has at least 5 times binding affinity for an antigen that does a parental antibody. The polypeptides have a sequence that differs from the parental antibody by an amino acid substitution of at least one amino acid in a complementarity determining region, the amino acid encoded by a codon that comprises a nucleotide belonging to a hotspot motif selected from AGY ro RGYW, where R is A or G, Y is C or T, and W is A or T. The amino acid substitutions can occur in the CDR3 of the variable region of the heavy or of the light chain, or in the CDR1 or 2 of those variable regions. In some embodiments of the invention, the antigen in mesothelin, and the parental antibody is SSscFv, and the polypeptide has a sequence which differs from antibody SS by an amino acid substitution of at least one amino acid selected from S92, G93, and Y94 (that is, selected from the serine residue at position 92, the glycine residue at position 93, or the tyrosine at position 94, according to the standard numbering of amino acid residues for the SSscFv. See also FIG. 1).

In some preferred embodiments, the substitutions of the SSscFv CDR3 variable region of the light change are selected from G93K-Y94H (that is, the glycine at position 93 is changed to a lysine and the tyrosine at position 94 is changed to a histidine, these changes define the antibody styled "SS1"), S92G-G93F-Y94N (that is, the serine at position 92 is changed to a glycine, the glycine at position 93 is changed to a phenylalanine, and the tyrosine at position 94 is changed to an asparagine; these changes define the scFv called "D8", and S92G-G93S—Y94H (that is, the serine at position 92 is changed to a glycine, the glycine at position 93 is changed to a serine, and the tyrosine at position 94 is changed to an histidine; these changes define the scFv called "D8").

The polypeptides described above can also form part of an immunoconjugate. For example, they can comprise a therapeutic moiety or a detectable label. In some embodiments, the therapeutic moiety can be a toxic moiety, such as a Pseudomonas exotoxin, or a cytotoxic fragment thereof, such as PE38. The toxic moiety can also be diptheria toxin or a cytotoxic fragment thereof, saporin or a cytotoxic fragment thereof, pokeweed antiviral protein or a cytotoxic fragment thereof, ricin or a cytotoxic fragment thereof, or bryodin 1 or a cytotoxic fragment thereof. In another embodiment, the polypeptides can further comprise a surface protein of a bacteriophage.

In another aspect, the invention relates to nucleotides encoding polypeptides comprising a mutated antibody heavy chain variable region or a mutated antibody light chain variable region, or both, wherein the polypeptide has at least 5 times binding affinity for an antigen that does a parental antibody. The polypeptides also have a sequence that differs from the parental antibody by an amino acid substitution of at least one amino acid in a complementarity determining region, the amino acid encoded by a codon that comprises a nucleotide belonging to a hotspot motif selected from AGY or RGYW, where R is A or G, Y is C or T, and W is A or T. In some embodiments, the antigen is mesothelin, the parental antibody is antimesothelin antibody SS and the polypeptide has a sequence which differs from antibody SS by an amino acid substitution of at least one amino acid selected from S92, G93, and Y94. In a further embodiment, the substitutions are selected from G93K-Y94H(SS1), S92G-G93F-Y94N (D8), and S92G-G93S—Y94H(C10).

In yet another aspect, the present invention relates to expression cassettes encoding a promoter operably linked to one of the nucleic acid molecules described above.

In another aspect, the invention relates to a method of killing a malignant cell bearing an antigen, comprising contacting the cell with an immunotoxin comprising a targeting moiety and a toxic moiety, the targeting moiety comprising a mutated antibody heavy chain variable region or a mutated antibody light chain variable region, or both, the polypeptide having at least 5 times binding affinity for an antigen that does a parental antibody. The polypeptides further have a sequence that differs from the parental antibody by an amino acid substitution of at least one amino acid in a complementarity determining region, the amino acid encoded by a codon that comprises a nucleotide belonging to a hotspot motif selected from AGY or RGYW, where R is A or G, Y is C or T, and W is A or T. In some embodiments, the antigen is mesothelin. Further, in some embodiments, the targeting moiety is selected from the group consisting of SS1, D8, and C10.

The invention further provides an antibody designated E4 in which the CDR3 VL differs from parental antibody SS by a substitution of L96T. E4 can also be used as the targeting moiety of an immunoconjugate, such as an immunotoxin used, for example, to purge mesothelin-bearing cancer cell in vitro, or to inhibit or kill cancer cells in vivo.

In yet further aspects, the invention relates to methods of identifying a polypeptide which has a higher affinity for a target antigen than does a parental antibody, comprising contacting a polypeptide comprising a mutated antibody heavy chain variable region or a mutated antibody light chain variable region, or both, the polypeptide having at least 5 times binding affinity for an antigen that does a parental antibody, and the polypeptides having a sequence that differs from the parental antibody by an amino acid substitution of at least one amino acid in a complementarity determining region, the amino acid encoded by a codon that comprises a nucleotide belonging to a hotspot motif selected from AGY or RGYW, where R is A or G, Y is C or T, and W is A or T, with the target antigen under conditions appropriate for specific binding between an antibody and the target antigen, eluting the polypeptide under conditions which remove any antibody or fragment thereof which has not bound to the target antigen with an affinity higher than that of the parental antibody or fragment thereof, and determining whether the polypeptide is bound to the antigen, whereby binding identifies the polypeptide as having a higher affinity for the target than does the parental antibody.

The invention further relates to a method of making a library of of nucleic acids encoding mutated antibody variable domains comprising providing a nucleic acid molecule encoding an amino acid sequence of a $V_H$ or a $V_L$ domain of a parental antibody, the nucleic acid molecule comprising at least one parental hot spot codon comprising at least one nucleotide within a hot spot motif and generating a plurality of mutated nucleic acid molecules encoding mutated amino acid sequences that differ from the parental amino acid sequence wherein each mutated nucleic acid sequence comprises at least one mutated codon different than a parental hot spot codon encoding an amino acid, the mutated codon encoding an amino acid different than the amino acid encoded by the parental hot spot codon.

In some embodiments, the plurality of mutated nucleic acid molecules used in the method contains at least 19 members, wherein each of the 19 members encodes an amino acid sequence in which the amino acid encoded by the parental hot spot codon is replaced by a different natural amino acid. In still more embodiments, the method can involve a plurality of mutated nucleic acid molecules which comprise mutated codons different than at least two parental hot spot codons encoding amino acids, each of the mutated codons encoding an amino acid different than the amino acid encoded by the parental hot spot codon. In other embodiments, the method can involve a plurality of mutated nucleic acid molecules which comprises at least 399 members, each of which members encodes an amino acid sequence in which the amino acids encoded by the parental hot spot codons is replaced by a different natural amino acid. In further embodiments of the method, the parental antibody is of a class of antibodies having at least one conserved amino acid encoded by a codon, wherein the codon or codons encoding the conserved amino acids are not mutated. In yet further embodiments of this method, the hot spot motif is selected from the group consisting of AGCA, AGTT, AGCT, AGTA, GGCA, GGTT, GGCT, GGTA, AGC, and AGT. In yet more embodiments of the method, the mutated nucleic acid molecule comprises at least one mutated codon within a portion of the $V_H$ or the $V_L$ domain comprising a CDR. The CDR can be the CDR3 of the $V_H$ domain or the CDR3 of the $V_L$ domain.

BRIEF DESCRIPTION OF THE DRAWINGS

FIG. 1 contains the amino acid sequence of SS scFv (SEQ ID NO: 1) as deduced from its nucleotide sequence. In the scFv, $V_H$ is connected to $V_L$ by a linker peptide, GVGGSG$_4$SG$_4$S (SEQ ID NO:2). The framework regions, CDRs, and linker have been marked. H denotes the heavy chain; L denotes the light chain; FR denotes a framework region; CDR denotes a complementarity determining region.

FIG. 2A: This Figure shows, in separate rows, the amino acid numbering, nucleotide sequence, and amino acid sequence, of the CDR3 of the variable light chain of SS scFv. Top row: Amino acid residue numbers of the variable light chain CDR3 of parental scFv SS. Middle row: Nucleotide sequence (SEQ ID NO:3) encoding the amino acids in the CDR3 of scFv SS CDR3. Rectangles designate the tetranucleotide hotspot motifs; an oval designates the serine hotspot motif in the sequence. Bottom row: Amino acid sequence (SEQ ID NO:4) of the CDR3 of scFv SS, in single letter code.

FIGS. 2B through 2E are panels representing the ELISA results of clones from individual libraries. Each symbol in a panel represents the ELISA signal of phage particles from a single clone. The filled squares in each panel (marked by arrows) represent the internal standard parental SS(scFv) phage. The libraries are designated at the top of each panel. FIG. 2B: ELISA results from library of clones mutated at residues 89, 93, and 94. FIG. 2C: ELISA results from library of clones mutated at residues 89, 90, and 91. FIG. 2D: ELISA results from library of clones mutated at residues 92, 93, and 94. FIG. 2E: ELISA results from library of clones mutated at residues 95, 96, and 97.

FIG. 3: Amino acid sequence of some of the ELISA positive phage clones obtained after panning of the different libraries. Only sequences of regions which differ among the clones are shown. An asterisk (*) indicates that several clones with the same amino acid sequence but different nucleotide sequences were found. VL CDR3 nucleotide (SEQ ID NO:3) and amino acid (SEQ ID NO:4) sequences are shown.

DETAILED DESCRIPTION OF THE INVENTION

I. Overview

Figure 1:
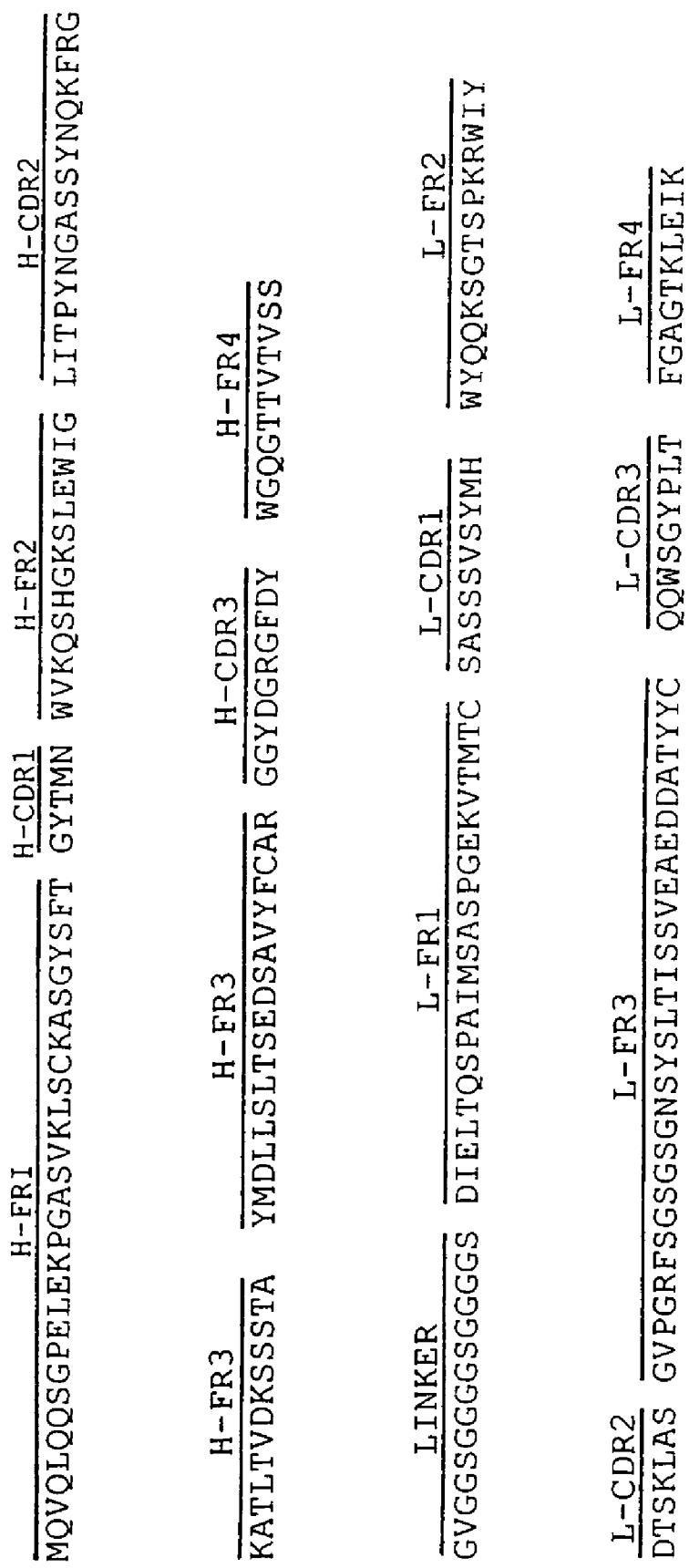
FIG. 1.

The present invention provides antibodies to mesothelin which have increased affinity for this antigen compared to SS(scFv). The antibodies can be used as targeting moieties to make more effective immunoconjugates, such as immunotoxins. These immunoconjugates can be used for in vitro uses, such as the detection of mesothelin-expressing cells present in a biological sample. The immunotoxins can further be used to kill cells expressing mesothelin, such as cancer cells of cancers expressing mesothelin on their surfaces.

The invention further provides a new method for generating antibodies with higher affinity to a target antigen than that of a parental antibody.

In particularly preferred embodiments, the antibody is a scFv or a dsFv. Many of the recombinant immunotoxins produced from constructs of scFv are one-third the size of IgG-toxin chemical conjugates and are homogeneous in composition. Elimination of the constant portion of the IgG molecule from the scFv results in faster clearance of the immunotoxin after injection into animals, including primates, and the smaller size of the conjugates improves drug penetration in solid tumors. Together, these properties lessen the side effects associated with the toxic moiety by reducing the time in which the immunotoxin (IT) interacts with non-target tissues and tissues that express very low levels of antigen.

These advantages, however, are offset to some degree by the loss of antigen binding affinity that occurs when IgGs are converted to scFvs (Reiter et al., *Nature Biotechnol.* 14:239–1245 (1996)). Increasing affinity has been shown to improve selective tumor delivery of scFvs (Adams et al., *Cancer Res.* 58:485–490 (1998)), and is likely to increase their usefulness in tumor imaging and treatment. Therefore, increasing the affinity of scFvs and other targeting moieties (such as dsFvs, Fabs. and F(ab')$_2$ of immunoconjugates is desirable to improve the efficiency of these agents in delivering effector molecules, such as toxins and other therapeutic agents, to their intended targets.

Improvements in affinity can be achieved in vitro by site directed or random mutagenesis. While antibody-antigen crystal structure can indicate which residues should be mutated to improve binding, atomic resolution structural data are not available for most antibodies. Therefore several strategies based on phage display technology have been developed to select higher affinity antibodies from libraries expressing mutated variants of Fabs and scFvs (Gram et al., *Proc. Natl. Acad. Sci. USA* 89:3576–3580 (1992); Low et al., *J. Mol. Biol.* 260:359–368 (1996); de Kruif et al., *J. Mol. Biol.* 248:97–105 (1995); Griffith et al, *EMBO J.* 12:725–734 (1993); Barbas et al., *J. Mol. Biol.* 230:812–823 (1993); Schier et al., *J. Mol. Biol.* 255: 28–43 (1996); Yelton et al, *J. Immunol.,* 155:1994–2004 (1995); Yang et al., *J. Mol. Biol.* 254:392403 (1995); Pini et al, *J. Biol. Chem.* 273:21769–21776 (1998); Wu et al., *Proc. Natl. Acad. Sci. USA* 95:6037–6042 (1998)). These approaches require the construction of huge and multiple libraries which are often difficult to attain and may be expensive to produce.

We have developed a new method that permits the generation of Fvs with increased affinity from a small library of variants. The method is based on the fact that the DNA encoding the variable regions of antibodies contain mutational hotspots, which are nucleotide sequences where mutations are frequently concentrated during the in vivo affinity maturation process (Neuberger and Milstein, *Curr. Biol.* 7: 248–254 (1995); Jolly et al., *Semin. Immunol.* 8:159–168 (1996); Gonzalez-Femandez et al., *Proc. Natl. Acad. Sci. USA* 91:12614–12618 (1994)). Several different types of variable region hotspots, such as direct and inverted repeats, palindromes, secondary structures and certain consensus sequences have been proposed (Neuberger and Milstein, *Curr. Biol.* 7: 248–254 (1995); Jolly et al., *Semin. Immunol.* 8:159–168 (1996); Gonzalez-Femandez et al., *Proc. Natl. Acad. Sci. USA* 91:12614–12618 (1994); Golding et al., *Genetics,* 115:169–176 (1987); Kolchanov et al., *FEB Lett.* 214:87–91 (1987); Rogozin et al., *Biochim. Biophys. Acta* 1089:175–182 (1991); Insel and Varade, *Int. Immunol.,* 6:1437–1443 (1994); Wagner el al., *Nature,* 376:732 (1995)). Among all these, the consensus hotspot sequences have been studied in more detail. One of these consensus sequences is a tetranucleotide A/G-G-C/T-A/T (Pu-G-Py-A/T). The other type is represented by the serine codons AGY, where Y can be a C or a T (Wagner et al., *Nature,* 376:732 (1995); Goyenechea and Milstein, *Proc. Natl. Acad. Sci. USA* 93:13979–13984 (1996)).

Recently, we developed a single chain Fv termed SS(scFv), which was selected from a phage display library based on its recognition of the mesothelin antigen expressed on the surface of ovarian cancers, mesotheliomas and several other human cancers (Chowdhury 1998; Chang and Pastan, *Proc. Natl. Acad. Sci. USA* 93:136–140 (1996)). The amino acid sequence of SS(scFv), as deduced from its nucleotide sequence, is set forth as FIG. 1, and the nucleotide sequence has been deposited in GenBank. SS(scFv) can be synthesized by recombinant means or, if desired, by standard techniques for synthesizing proteins.

SS(scFv)-PE38 is an immunotoxin made by fusing SS(scFv) with a 38 kDa truncated mutant of *Pseudomonas* exotoxin A called PE38. When injected into mice carrying mesothelin-positive human tumors, SS(scFv)-PE38 causes regressions of the tumors and is being developed for treating human cancers. The affinity of SS (scFv)—PE38 for mesothelin was found to be 11 nM (Chowdhury 1998). Although this is a relatively high affinity, even higher affinities are considered desirable to enhance the performance of immunoconjugates based on the SS antibody, including the SS(scFv), in therapeutic, diagnostic, and in vitro uses.

Prior attempts to improve antibody affinity have relied, inter alia, on random mutations of the residues of CDRs or on mutating particular amino acids found from crystallagraphic analysis to affect antigen contact. Improving affinity through immunization and DNA immunization also appeared unlikely in view of the results reported in Chowdhury 1998. To overcome some of the disadvantages in these methods, noted above, we created a new approach. We targeted hotspots in the CDRs, where we created random mutations. Although any CDR could be altered in this approach, we tested the method using the CDR3 of the variable region light chain. In part, CDR3 was chosen because it is centrally located in the antigen binding site and has the greatest impact on antigen recognition and affinity. CDRs 2 and 1 are, however, also known to affect antigen affinity (in the order stated), and could be used instead of or in addition to CDR3.

Using this approach we were able to generate and to isolate scFvs that had increases in affinity of from 15 to 55-fold from a small library of only about 8000 independent clones. Immunotoxins made with these high affinity variants had more than a 10-fold increase in cytotoxic activity. Although we used the light chain CDR3 in the studies reported in detail below, we have used the same approach to generate scFvs from the heavy chain CDR3 of SS. Like the scFV generated by mutating the SS light chain CDR3, in ELISA binding studies, a number of these mutated heavy chain scFV show a higher affinity for mesothelin than does the parental SS scFV. Moreover, we have also used the technique to an antibody other than SS, in this case, an antibody which binds to a mutant form of epidermal growth factor. In light of these results, we expect this approach to be generally useful in rapidly obtaining Fvs, Fabs or other recombinant antibodies with increased affinity for their target antigens compared to the affinity of their parental antibodies. In the course of this work, we also generated an scFv, designated E4, made by a mutation outside a hotspot motif, with an affinity for mesothelin about 3.7 times that of SS. While its affinity is markedly less than that of scFvs made by the hotspot mutation method, its affinity is still several times greater than that of the best previously known anti-mesothelin scFv.

In the sections below, the terms used herein are defined for additional clarity. The method is described in more detail. Finally, the examples set forth specific experimental procedures for conducting the method and the sequences of the CDR3 of specific improved anti-mesothelin antibodies.

II. Definitions

Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

The term "mesothelin" includes reference to a mesothelin protein and fragments thereof which may be present on the surface of cells of a mammal, such as a rat, a mouse, a primate, or, in particular, a human. The preferred nucleic acid and amino acid sequences of mesothelin are as described in PCT published application WO 97/25,068, U.S. application Ser. No. 08/776,271, now U.S. Pat. No. 6,083, 502, and U.S. Provisional Application 60/010,166. In addition, see, Chang, K. & Pastan, I., *Int. J. Cancer* 57:90 (1994); Chang, K. & Pastan, I., *Proc. Nat'l Acad. Sci. USA* 93:136 (1996); Brinkmann U., et al., *Int. J. Cancer* 71:638 (1997); and Chowdhury, P. S., et al., *Mol. Immunol.* 34:9 (1997). Mesothelin also refers to mesothelin proteins or peptides which remain intracellular, as well as secreted or isolated extracellular protein.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies), heteroconjugate antibodies (e.g., bispecific antibodies) and recombinant single chain Fv fragments (scFv), disulfide stabilized (dsFv) Fv fragments (See, U.S. Ser. No. 08/077,252, incorporated herein by reference), or pFv fragments (See, U.S. Provisional Patent Applications 60/042,350 and 60/048,848). The term "antibody" also includes antigen binding forms of antibodies (e.g., Fab', F(ab')$_2$, Fab, Fv and rIgG. See also, Pierce Catalog and Handbook, 1994–1995 (Pierce Chemical Co., Rockford, Ill.); Kuby, J., *Immunology*, 3$^{rd}$ Ed., W.H. Freeman & Co., New York (1997).

An antibody immunologically reactive with a particular antigen can be generated by recombinant methods such as selection of libraries of recombinant antibodies in phage or similar vectors, see, e.g., Huse, et al., *Science* 246:1275–1281 (1989); Ward, et al., *Nature* 341:544–546 (1989); and Vaughan, et al., *Nature Biotech.* 14:309–314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined (see, Kabat, E., et al., SEQUENCES OF PROTEINS OF IMMUNOLOGICAL INTEREST, U.S. Department of Health and Human Services, (1987), which is hereby incorporated by reference). The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a V$_H$ CDR3 is located in the variable domain of the heavy chain of the antibody in which it is found, whereas a V$_L$ CDR1 is the CDR1 from the variable domain of the light chain of the antibody in which it is found.

References to "V$_H$" or a "VH" refer to the variable region of an immunoglobulin heavy chain, including an Fv, scFv, dsFv or Fab. References to "V$_L$" or a "VL" refer to the variable region of an immunoglobulin light chain, including of an Fv, scFv, dsFv or Fab The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable domain of the heavy chain to the variable domain of the light chain.

The term "parental antibody" means any antibody of interest which is to be mutated or varied to obtain antibodies or fragments thereof which bind to the same epitope as the parental antibody, but with higher affinity.

The term "hotspot" means a portion of a nucleotide sequence of a CDR or of a framework region of a variable domain which is a site of particularly high natural variation. Although CDRs are themselves considered to be regions of hypervariability, it has been learned that mutations are not evenly distributed throughout the CDRs. Particular sites, or hotspots, have been identified as these locations which undergo concentrated mutations. The hotspots are characterized by a number of structural features and sequences. These "hotspot motifs" can be used to identify hotspots. Two consensus sequences motifs which are especially well characterized are the tetranucleotide sequence RGYW and the serine sequence AGY, where R is A or G, Y is C or T, and W is A or T.

A "targeting moiety" is the portion of an immunoconjugate intended to target the immunoconjugate to a cell of interest. Typically, the targeting moiety is an antibody, a scFv, a dsFv, an Fab, or an F(ab')$_2$.

A "toxic moiety" is the portion of a immunotoxin which renders the immunotoxin cytotoxic to cells of interest.

A "therapeutic moiety" is the portion of an immunoconjugate intended to act as a therapeutic agent.

The term "therapeutic agent" includes any number of compounds currently known or later developed to act as anti-neoplastics, anti-inflammatories, cytokines, anti-infectives, enzyme activators or inhibitors, allosteric modifiers, antibiotics or other agents administered to induce a desired therapeutic effect in a patient. The therapeutic agent may also be a toxin or a radioisotope, where the therapeutic effect intended is, for example, the killing of a cancer cell.

A "detectable label" means, with respect to an immunoconjugate, a portion of the immunoconjugate which has a property rendering its presence detectable. For example, the immunoconjugate may be labeled with a radioactive isotope which permits cells in which the immunoconjugate is present to be detected in immunohistochemical assays.

The term "effector moiety" means the portion of an immunoconjugate intended to have an effect on a cell targeted by the targeting moiety or to identify the presence of the immunoconjugate. Thus, the effector moiety can be, for example, a therapeutic moiety, a toxin, a radiolabel, or a fluorescent label.

The term "immunoconjugate" includes reference to a covalent linkage of an effector molecule to an antibody. The effector molecule can be an immunotoxin.

The terms "effective amount" or "amount effective to" or "therapeutically effective amount" includes reference to a dosage of a therapeutic agent sufficient to produce a desired result, such as inhibiting cell protein synthesis by at least 50%, or killing the cell.

The term "toxin" includes reference to abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE or the B chain of DT) and replacing it with a different targeting moiety, such as an antibody.

The term "contacting" includes reference to placement in direct physical association.

An "expression plasmid" comprises a nucleotide sequence encoding a molecule or interest, which is operably linked to a promoter.

As used herein, the term "anti-mesothelin" in reference to an antibody, includes reference to an antibody which is generated against mesothelin. In preferred embodiments, the mesothelin is a primate mesothelin such as human mesothelin. In a particularly preferred embodiment, the antibody is generated against human mesothelin synthesized by a non-primate mammal after introduction into the animal of cDNA which encodes human mesothelin.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table 1:

TABLE 1

Amino Acid Nomenclature

| Name | 3-letter | 1-letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S-Me) | — |
| Norleucine | Nle | — |

TABLE 1-continued

Amino Acid Nomenclature

| Name | 3-letter | 1-letter |
|---|---|---|
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table 2 each contain amino acids that are conservative substitutions for one another:

TABLE 2

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, PROTEINS, W. H. Freeman and Company, New York (1984).

The terms "substantially similar" in the context of a peptide indicates that a peptide comprises a sequence with at least 90%, preferably at least 95% sequence identity to the reference sequence over a comparison window of 10–20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1–2 kcal/mol for a hydrogen bond. In the context of this invention, the cysteines which form the disulfide bond are within the framework regions of the single chain antibody and serve to stabilize the conformation of the antibody.

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and ftmgal mitochondria, the bacterium *Mycoplasma capricolum* (*Proc. Nat'l Acad. Sci. USA* 82:2306–2309 (1985), or the ciliate *Macronucleus*, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The phrase "phage display library" refers to a population of bacteriophage, each of which contains a foreign cDNA recombinantly fused in frame to a surface protein. The phage display the foreign protein encoded by the cDNA on its surface. After replication in a bacterial host, typically *E. coli*, the phage which contain the foreign cDNA of interest are selected by the expression of the foreign protein on the phage surface.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403–410 and Altschuel et al. (1977) *Nucleic Acids Res.* 25: 3389–3402, respectively. Software for performing BLAST analyses is publicly available through the National Center for Biotechnology Information which can be found on the web by entering "www.", followed by: ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word bits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

As used herein, "mammalian cells" includes reference to cells derived from mammals including humans, rats, mice, guinea pigs, chimpanzees, or macaques. The cells may be cultured in vivo or in vitro.

The term "selectively reactive" refers, with respect to an antigen, the preferential association of an antibody, in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 2-fold, preferably greater than 5-fold, more preferably greater than 10-fold and most preferably greater than 100-fold increase in amount of bound antibody (per unit time) to a cell or tissue bearing mesothelin as compared to a cell or tissue lacking mesothelin. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The terms "SS" or "SS(scFv)" refer to an scFv that binds to mesothelin with high affinity and which has the amino acid sequence set forth in FIG. 1. See, Chowdhury 1998.

III. Generation of Antibodies with Higher Affinities

As described above, the present invention provides a new method for generating from a parental antibody one or more mutant antibodies with a higher affinity for a target antigen than that of the parental antibody. In contrast to prior techniques, which created mutations randomly within a CDR, we have found that we can obtain higher affinity antibodies with markedly less effort by targeting mutations to codons which contain at least one nucleotide within a hot spot motif (for ease of reference, these will be termed "hot spot codons" for this discussion). Multiple iterations of the mutations are made so that the mutations result in the hot spot codon being replaced (one at a time) by codons encoding each of the 19 other natural amino acids. Conveniently, this can be done by randomizing the process so that mutations result in codons encoding all 20 amino acids (including the original one) randomly appear in place of the original hot spot codon (that is, that an alanine is replaced in one mutated form with a glycine, in another with an arginine, in a third with cysteine, and so on).

CDRs typically contain more than one hot spot codon. One, two, three, or more such codons can be mutated within a CDR to generate obtain antibodies with higher affinity. Our results indicate that better results may be obtained by mutating three hot spot codons at a time than by mutating two such codons.

Hot spot codons in any CDR can be mutated to created higher affinity antibodies. If desired, one or more hot spot codons in one CDR can be mutated at the same time as one or more hot spot codons from one of the other CDRs. It should be noted that each antibody contains only six CDRs, that the CDRs are of limited length (for example, as shown in FIG. 1, the CDRs of SSscFv range from 5 to 17 amino acids in length), and that only some of the codons encoding those amino acids contain a nucleotide located within a hot spot motif. For example, FIG. 2A shows that only 5 of the 9 amino acids in the VL CDR3 of SSscFv are encoded by hot spot codons.

The framework regions of the variable domain contribute modestly to antibody-antigen binding interactions. Optionally, hot spot codons in the framework regions can be mutated to make further improvements in binding affinity.

Kabat, supra, provides information about the classification of antibody heavy and light chains into subgroups and families. For example, under Kabat's classification, the $V_H$ of SSscFv belongs to subgroup IIA and family V and the $V_L$ belongs to subgroup VI and family XI. It is known in the art that amino acid residues at certain locations are conserved in particular subgroups. See, e.g., Johnson et al., in *WEIR'S HANDBOOK OF EXPERIMENTAL IMMUNOLOGY I. IMMUNOCHEMISTRY AND MOLECULAR IMMUNOLOGY*, 5$^{th}$ Ed., Herzenberg et al. eds., Blackwell Science Inc., Cambridge, Mass., Chapter 6, pp. 6.1–6.21 (1996) (the entirety of Weir's Handbook is hereby incorporated by reference). Our results show that it is preferable not to mutate codons encoding these conserved residues even if the codons contain a nucleotide within a hot spot motif and would otherwise be candidates for mutation.

The Examples below demonstrate the use of these principles to generate antibodies with mutated hot spot codons. We selected the anti-mesothelin antibody SSscFv as a model antibody in part because immunotoxins using it as a targeting moiety have shown good effect on human tumors in animal models. We selected the CDR3s because of they are the major site of antigen interaction. We chose the variable light chain over the heavy chain because we viewed it as likely that the light chain is less optimized for antigen affinity during normal affinity maturation than is the heavy chain. The CDR3 of the light chain of SSscFv contains 9 amino acid residues, which by convention are numbered 89 through 97 (see FIG. 2A). A library was made in which three codons in two tetranucleotide hotspot motifs were simultaneously mutated (residues 89, 93, and 94) and a library was made in which a serine hotspot codon and codons in a tetranucleotide hotspot motif were simultaneously mutated (residues 92, 93 and 94). When clones from these libraries were screened for their affinity to the antigen, most of the mutants in these libraries displayed higher affinities to the antigen than did the parental antibody, SSscFv. By contrast, control libraries containing mutations in the residue, Q90, which is conserved in light chain of the subgroup in which SSscFv is classified, resulted in mutants with affinities about the same or lower than those of the parental antibody. See, FIG. 2C. Similarly, a library in which mutations were made in codons which did not contain a nucleotide within a hotspot showed affinities for the antigen about the same or modestly better than the original parental SSscFv. See, FIG. 2E.

Affinity binding studies confirmed that there was a striking difference in the affinity of the mutated antibodies. ScFv generated by mutating hotspot codons which do not encode a conserved residue resulted in generating several antibodies which had affinities to the target antigen ranging from 15 times to as much as 55 times higher than that of the already-high affinity parental antibody from which they were derived. In contrast, the best clone resulting from mutations of amino acids encoded by codons which did not have at least one nucleotide within a hotspot motif had an increase in affinity of only 3.7 fold. And, the generation and screening of these high affinity antibodies required libraries of sizes orders of magnitude lower than those required for previous methods involving CDR mutations.

The mutated antibody with the highest affinity, designated C10, has the amino acid sequence of the parental SSscFv, except for residues 92, 93, and 94. At location 92, the "S" (serine) of the SSscFv is changed to a "G" (glycine). At position 93, the "G" of the SSscFv sequence is changed to an "S." At position 94, the "Y" (tyrosine) is changed to a "H" (histidine). The changes for each mutant clone, including the other two high affinity clones, SS1 and D8, are set forth in FIG. 3. By convention, these amino acid substitutions can also be described in a shorthand form in which the amino acid in the original sequence is listed by its single letter code, followed by its position number and the standard single letter code for the amino acid which replaces it in the changed sequence. Thus, the changes for clone C10, described above, can also be written as S92G-G93S-Y94H. Similarly, the scFv of clone SS I can be described as G93K-Y94H and the scFv of clone D8 by S92G-G93F-Y94N. The scFv of the E4 clone, which did not have a nucleotide mutated within a hotspot motif, can be described as L96T.

IV. Anti-Mesothelin Antibodies

The present invention provides antibodies which bind to mesothelin with higher affinity than prior art antibodies. In particular, the invention provides antibodies, which we have designated as SS1, C10, and D8, which have affinities for mesothelin 15, 55, and 37 times higher, respectively, than the affinity of their parental antibody, SS(scFv). SS(scFv) was previously the highest affinity antibody known which is specifically reactive with mesothelin. The invention further provides a method for generating other high affinity antibodies against mesothelin and other antigens of interest. The immunoconjugates disclosed below target mesothelin using antibodies of the present invention. These antibodies are selectively reactive under immunological conditions to those determinants of mesothelin displayed on the surface of mammalian cells and are accessible to the antibody from the extracellular milieu. The invention further provides an antibody designated E4 which, although not generated by the methods of the invention and not of as high an affinity for mesothelin as antibodies generated by the methods of the invention, still has an affinity for mesothelin some 3.7 times that of SS.

The anti-mesothelin antibodies generated in the present invention can be linked to effector molecules (EM) through the EM carboxyl terminus, the EM amino terminus, through an interior amino acid residue of the EM such as cysteine, or any combination thereof. Similarly, the EM can be linked directly to the heavy, light, Fc (constant region) or framework regions of the antibody. Linkage can occur through the antibody's amino or carboxyl termini, or through an interior amino acid residue. Further, multiple EM molecules (e.g., any one of from 2–10) can be linked to the anti-mesothelin antibody and/or multiple antibodies (e.g., any one of from 2–5) can be linked to an EM. The antibodies used in a multivalent immunoconjugate composition of the present invention can be directed to the same or different mesothelin epitopes.

In preferred embodiments of the present invention, the anti-mesothelin antibody is a recombinant antibody such as a scFv or a disulfide stabilized Fv antibody. Fv antibodies are typically about 25 kDa and contain a complete antigen-binding site with 3 CDRs per heavy and light chain. If the $V_H$ and the $V_L$ chain are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker.

In a particularly preferred embodiment, the antibody is a single chain Fv (scFv). The $V_H$ and the $V_L$ regions of a scFv antibody comprise a single chain which is folded to create an antigen binding site similar to that found in two chain antibodies. Once folded, noncovalent interactions stabilize the single chain antibody. In a more preferred embodiment, the scFv is recombinantly produced. In yet another preferred embodiment, the $V_H$ region has the amino acid sequence as shown in FIG. 1. One of skill will realize that conservative variants of the antibodies of the instant invention can be made. Such conservative variants employed in scFv fragments will retain critical amino acid residues necessary for correct folding and stabilizing between the $V_H$ and the $V_L$ regions.

In some embodiments of the present invention, the scFv antibody is directly linked to the EM through the light chain. However, scFv antibodies can be linked to the EM via its amino or carboxyl terminus.

While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston, et al., *Proc. Nat'l Acad. Sci. USA* 8:5879 (1988); Bird, et al., *Science* 242:4236 (1988); Glockshuber, et al., *Biochemistry* 29:1362 (1990); U.S. Pat. No. 4,946,778, U.S. Pat. No. 5,132,405 and Stemmer, et al., *Biotechniques* 14:256–265 (1993), all incorporated herein by reference. Generally the peptide linker will have no specific biological activity other than to join the regions or to preserve some minimum distance or other spatial relationship between them. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Ser (SEQ ID NO:5), preferably 2, 3, 4, 5, or 6 such sequences. However, it is to be appreciated that some amino acid substitutions within the linker can be made. For example, a valine can be substituted for a glycine.

A. Antibody Production

Methods of producing polyclonal antibodies are known to those of skill in the art. In brief, an immunogen, preferably isolated mesothelin or extracellular mesothelin epitopes are mixed with an adjuvant and animals are immunized with the mixture. When appropriately high titers of antibody to the immunogen are obtained, blood is collected from the animal and antisera are prepared. If desired, further fractionation of the antisera to enrich for antibodies reactive to the polypeptide is performed. See, e.g., Coligan, CURRENT PROTOCOLS IN IMMUNOLOGY, Wiley/Greene, N.Y. (1991); and Harlow & Lane, supra, which are incorporated herein by reference.

Monoclonal antibodies may be obtained by various techniques familiar to those skilled in the art. Description of techniques for preparing such monoclonal antibodies may be found in, e.g., Stites, et al. (eds.) BASIC AND CLINICAL IMMUNOLOGY (4TH ED.), Lange Medical Publications, Los Altos, Calif., and references cited therein; Harlow & Lane, supra; Goding, MONOCLONAL ANTIBODIES: PRINCIPLES AND PRACTICE (2D ED.), Academic Press, New York, N.Y. (1986); Kohler & Milstein, *Nature* 256:495–497 (1975); and particularly (Chowdhury, P. S., et al., *Mol. Immunol.* 34:9 (1997)), which discusses one method of generating monoclonal antibodies.

It is preferred that parental monoclonal antibodies are made by immunizing an animal with the target antigen or with nucleic acid sequence that encodes the desired immunogen, such as mesothelin. Immunization with non-replicating transcription units that encode a heterologous proteins elicits antigen specific immune responses. After translation into the foreign protein, the protein is processed and presented to the immune system like other cellular proteins. Because it is foreign, an immune response is mounted against the protein and peptide epitopes that are derived from it (Donnelly, et al. *J. Immunol. Methods* 176:145–152 (1994); and Boyer, et al, *J. Med. Primatol.* 25:242–250 (1996)). This technique has two significant advantages over protein-based immunization. One is that it does not require the purification of the protein, which at best, is time consuming and in cases of many membrane proteins, is very difficult. A second advantage is that since the immunogen is synthesized in a mammalian host, it undergoes proper post-translational modifications and folds into the native structure.

To immunize with mesothelin-coding DNA, mesothelin-coding cDNA is introduced into a plasmid so that transcription of the coding sequence is under the control of a promoter such as the CMV promoter. The plasmid is then injected into an animal, either subcutaneously, intradermally, intraperitoneally, etc. As a result, the mesothelin cDNA is transcribed in the animal into mRNA, mesothelin is translated from the mRNA, the translated protein undergoes proper post-translational modifications and is expressed on the surface of cells which synthesized mesothelin. The animal raises antibodies to mesothelin and the sera is monitored for antibody titer.

Optionally, in addition to the coding region and regulatory elements, the plasmid carries an ampicillin resistance (Amp) gene. The Amp gene is known to have immunostimulatory sequences for Th1 responses necessary for increased antibody production (Sato, et al., *Science* 273:352–354 (1996)).

As described above, in preferred embodiments, the monoclonal antibody is a scfv. Methods of making scfv antibodies have been described. See, Huse, et al., supra; Ward, et al. *Nature* 341:544–546 (1989); and Vaughan, et al., supra. In brief, mRNA from B-cells is isolated and cDNA is prepared. The cDNA is amplified by well known techniques, such as PCR, with primers specific for the variable regions of heavy and light chains of immunoglobulins. The PCR products are purified by, for example, agarose gel electrophoresis, and the nucleic acid sequences are joined. If a linker peptide is desired, nucleic acid sequences that encode the peptide are inserted between the heavy and light chain nucleic acid sequences. The sequences can be joined by techniques known in the art, such as blunt end ligation, insertion of restriction sites at the ends of the PCR products or by splicing by overlap extension (Chowdhury, et al., *Mol. Immunol.* 34:9 (1997)). After amplification, the nucleic acid which encodes the scFv is inserted into a vector, again by techniques well known in the art. Preferably, the vector is capable of replicating in prokaryotes and of being expressed in both eukaryotes and prokaryotes.

In a preferred embodiment, scFv are chosen through a phage display library. The procedure described above for synthesizing scFv is followed. After amplification by PCR, the scFv nucleic acid sequences are fused in frame with gene III (gIII) which encodes the minor surface protein gIIIp of the filamentous phage (Marks, et al., *J. Biol. Chem.* 267: 16007–16010 (1992); Marks, et al., *Behring Inst. Mitt.* 91:6–12 (1992); and Brinkmann, et al., *J. Immunol Methods* 182:41–50 (1995)). The phage express the resulting fusion protein on their surface. Since the proteins on the surface of the phage are functional, phage bearing mesothelin-binding antibodies can be separated from non-binding or lower affinity phage by panning or antigen affinity chromatography (McCafferty, et al., *Nature* 348:552–554 (1990)).

In a preferred embodiment, scFv that specifically bind to mesothelin are found by panning. Panning is done by coating a solid surface with mesothelin and incubating the phage on the surface for a suitable time under suitable conditions. The unbound phage are washed off the solid surface and the bound phage are eluted. Finding the antibody with the highest affinity is dictated by the efficiency of the selection process and depends on the number of clones that can be screened and the stringency with which it is done. Typically, higher stringency corresponds to more selective panning. If the conditions are too stringent, however, the phage will not bind. After one round of panning, the phage that bind to mesothelin coated plates are expanded in *E. coli* and subjected to another round of panning. In this way, an enrichment of 2000-fold occurs in 3 rounds of panning. Thus, even when enrichment in each round is low, multiple rounds of panning will lead to the isolation of rare phage and the genetic material contained within which encodes the sequence of the highest affinity antibody. The physical link between genotype and phenotype provided by phage display makes it possible to test every member of a cDNA library for binding to antigen, even with large libraries of clones.

B. Binding Affinity of Antibodies

The antibodies of this invention bind to their target antigens with an affinity at least 5 times better than that of their parental antibodies. In one embodiment, the antibodies are anti-mesothelin antibodies which bind to an extracellular epitope of mesothelin. Binding affinity for a target antigen is typically measured or determined by standard antibody-antigen assays, such as competitive assays, saturation assays, or immunoassays such as ELISA or RIA.

Such assays can be used to determine the dissociation constant of the antibody. The phrase "dissociation constant" refers to the affinity of an antibody for an antigen. Specificity of binding between an antibody and an antigen exists if the dissociation constant ($K_D$=1/K, where K is the affinity constant) of the antibody is <1 μM, preferably <100 nM, and most preferably <0.1 nM. Antibody molecules will typically have a $K_D$ in the lower ranges. $K_D$=[Ab–Ag]/[Ab][Ag] where [Ab] is the concentration at equilibrium of the antibody, [Ag] is the concentration at equilibrium of the antigen and [Ab–Ag] is the concentration at equilibrium of the antibody-antigen complex. Typically, the binding interactions between antigen and antibody include reversible non-covalent associations such as electrostatic attraction, Van der Waals forces and hydrogen bonds. This method of defining binding specificity applies to single heavy and/or light chains, CDRs, fusion proteins or fragments of heavy and/or light chains, that are specific for mesothelin if they bind mesothelin alone or in combination.

C. Immunoassays

The antibodies can be detected and/or quantified using any of a number of well recognized immunological binding assays (see, e.g., U.S. Pat. Nos. 4,366,241; 4,376,110; 4,517,288; and 4,837,168). For a review of the general immunoassays, see also METHODS IN CELL BIOLOGY, VOL. 37, Asai, ed. Academic Press, Inc. New York (1993); BASIC AND CLINICAL IMMUNOLOGY 7TH EDITION, Stites & Terr, eds. (1991). Immunological binding assays (or immunoassays) typically utilize a ligand (e.g., mesothelin) to specifically bind to and often immobilize an antibody. The antibodies employed in immunoassays of the present invention are discussed in greater detail supra.

Immunoassays also often utilize a labeling agent to specifically bind to and label the binding complex formed by the ligand and the antibody. The labeling agent may itself be one of the moieties comprising the antibody/analyte complex, i.e., the anti-mesothelin antibody. Alternatively, the labeling agent may be a third moiety, such as another antibody, that specifically binds to the antibody/mesothelin protein complex.

In one aspect, a competitive assay is contemplated wherein the labeling agent is a second anti-mesothelin antibody bearing a label. The two antibodies then compete for binding to the immobilized mesothelin. Alternatively, in a non-competitive format, the mesothelin antibody lacks a label, but a second antibody specific to antibodies of the species from which the anti-mesothelin antibody is derived, e.g., murine, and which binds the anti-mesothelin antibody, is labeled.

Other proteins capable of specifically binding immunoglobulin constant regions, such as Protein A or Protein G may also be used as the label agent. These proteins are normal constituents of the cell walls of streptococcal bacteria. They exhibit a strong non-immunogenic reactivity with immunoglobulin constant regions from a variety of species (see, generally Kronval, et al., *J. Immunol.* 111: 1401–1406 (1973); and Akerstrom, et al., *J. Immunol.* 135: 2589–2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antibody, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting anti-mesothelin antibodies in a sample containing the antibodies generally comprises the steps of contacting the sample with an antibody which specifically reacts, under immunologically reactive conditions, to the mesothelin/antibody complex.

V. Production of Immunoconjugates

Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents may include various drugs such as vinblastine, daunomycin and the like, cytotoxins such as native or modified *Pseudomonas* exotoxin or Diphtheria toxin, encapsulating agents, (e.g., liposomes) which themselves contain pharmacological compositions, radioactive agents such as $^{125}I$, $^{32}P$, $^{14}C$, $^{3}H$ and $^{35}S$ and other labels, target moieties and ligands.

The choice of a particular therapeutic agent depends on the particular target molecule or cell and the biological effect is desired to evoke. Thus, for example, the therapeutic agent may be a cytotoxin which is used to bring about the death of a particular target cell. Conversely, where it is merely desired to invoke a non-lethal biological response, the therapeutic agent may be conjugated to a non-lethal pharmacological agent or a liposome containing a non-lethal pharmacological agent.

With the therapeutic agents and antibodies herein provided, one of skill can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

A. Recombinant Methods

The nucleic acid sequences of the present invention can be prepared by any suitable method including, for example, cloning of appropriate sequences or by direct chemical synthesis by methods such as the phosphotriester method of Narang, et al., *Meth. Enzymol.* 68:90–99 (1979); the phosphodiester method of Brown, et al., *Meth. Enzymol.* 68:109–151 (1979); the diethylphosphoramidite method of Beaucage, et al., *Tetra. Lett.* 22:1859–1862 (1981); the solid phase phosphoramidite triester method described by Beaucage & Caruthers, *Tetra. Letts.* 22(20):1859–1862 (1981), e.g., using an automated synthesizer as described in, for example, Needham-VanDevanter, et al. *Nucl. Acids Res.* 12:6159–6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., MOLECULAR CLONING: A LABORATORY MANUAL (2ND ED.), Vols. 1–3, Cold Spring Harbor Laboratory (1989)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding native EM or anti-mesothelin antibodies can be modified to form the EM, antibodies, or immunoconjugates of the present invention. Modification by site-directed mutagenesis is well known in the art. Nucleic acids encoding EM or anti-mesothelin antibodies can be amplified by in vitro methods. Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In a preferred embodiment, immunoconjugates are prepared by inserting the cDNA which encodes an anti-mesothelin scFv antibody into a vector which comprises the cDNA encoding the EM. The insertion is made so that the scFv and the EM are read in frame, that is in one continuous polypeptide which contains a functional Fv region and a functional EM region. In a particularly preferred embodiment, cDNA encoding a diphtheria toxin fragment is ligated to a scFv so that the toxin is located at the carboxyl terminus of the scFv. In a most preferred embodiment, cDNA encoding PE is ligated to a scFv so that the toxin is located at the amino terminus of the scFv.

Once the nucleic acids encoding an EM, anti-mesothelin antibody, or an immunoconjugate of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eucaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

One of skill would recognize that modifications can be made to a nucleic acid encoding a polypeptide of the present invention (i.e., anti-mesothelin antibody, PE, or an immunoconjugate formed from their combination) without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

In addition to recombinant methods, the immunoconjugates, EM, and antibodies of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3–284; Merrifield, et al. *J. Am. Chem. Soc.* 85:2149–2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

B. Purification

Once expressed, the recombinant immunoconjugates, antibodies, and/or effector molecules of the present invention can be purified according to standard procedures of the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies of this invention. See, Buchner, et al., *Anal. Biochem.* 205:263–270 (1992); Pluckthun, *Biotechnology* 9:545 (1991); Huse, et al., *Science* 246:1275 (1989) and Ward, et al., *Nature* 341:544 (1989), all incorporated by reference herein.

Often, functional heterologous proteins from *E. coli* or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al, *Biochemistry* 9: 5015–5021 (1970), incorporated by reference herein, and especially as described by Buchner, et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

VI. *Pseudomonas* Exotoxin and Other Toxins

Toxins can be employed with antibodies of the present invention to yield immunotoxins. Exemplary toxins include ricin, abrin, diphtheria toxin and subunits thereof, as well as botulinum toxins A through F. These toxins are readily available from commercial sources (e.g., Sigma Chemical Company, St. Louis, Mo.). Diphtheria toxin is isolated from *Corynebacterium diphtheriae*. Ricin is the lectin $RCA_{60}$ from *Ricinus communis* (Castor bean). The term also references toxic variants thereof. For example, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, *J. Biochim. Biophys. Acta* 266:543 (1972)). The A chain is responsible for inactivating protein synthesis and killing cells. The B chain binds ricin to cell-surface galactose residues and facilitates transport of the A chain into the cytosol (Olsnes, et al., *Nature* 249:627–631 (1974) and U.S. Pat. No. 3,060,165).

Abrin includes toxic lectins from Abrus precatorius. The toxic principles, abrin a, b, c, and d, have a molecular weight of from about 63 and 67 kD and are composed of two disulfide-linked polypeptide chains A and B. The A chain inhibits protein synthesis; the B-chain (abrin-b) binds to D-galactose residues (see, Funatsu, et al., *Agr. Biol. Chem.* 52:1095 (1988); and Olsnes, *Methods Enzymol.* 50:330–335 (1978)).

In preferred embodiments of the present invention, the toxin is *Pseudomonas* exotoxin (PE). The term "*Pseudomonas* exotoxin" as used herein refers to a full-length native (naturally occurring) PE or a PE that has been modified. Such modifications may include, but are not limited to, elimination of domain Ia, various amino acid deletions in domains Ib, II and III, single amino acid substitutions and the addition of one or more sequences at the carboxyl terminus such as KDEL (SEQ ID NO:6) and REDL (SEQ ID NO:7). See Siegall, et al., *J. Biol. Chem.* 264:14256–14261 (1989). In a preferred embodiment, the cytotoxic fragment of PE retains at least 50%, preferably 75%, more preferably at least 90%, and most preferably 95% of the cytotoxicity of native PE. In a most preferred embodiment, the cytotoxic fragment is more toxic than native PE.

Native *Pseudomonas* exotoxin A (PE) is an extremely active monomeric protein (molecular weight 66 kD), secreted by *Pseudomonas aeruginosa*, which inhibits protein synthesis in eukaryotic cells. The native PE sequence is provided in commonly assigned U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain la (amino acids 1–252) mediates cell binding. Domain II (amino acids 253–364) is responsible for translocation into the cytosol and domain III (amino acids 400–613) mediates ADP ribosylation of elongation factor 2. The function of domain Ib (amino acids 365–399) remains undefined, although a large part of it, amino acids 365–380, can be deleted without loss of cytotoxicity. See Siegall, et al., (1989), supra.

PE employed in the present invention include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (e.g., as a protein or pre-protein). Cytotoxic fragments of PE include PE40, PE38, and PE35.

In preferred embodiments, the PE has been modified to reduce or eliminate non-specific cell binding, frequently by deleting domain Ia. as taught in U.S. Pat. No. 4,892,827, although this can also be achieved, for example, by mutating certain residues of domain Ia. U.S. Pat. No. 5,512,658, for instance, discloses that a mutated PE in which Domain Ia is present but in which the basic residues of domain Ia at positions 57, 246, 247, and 249 are replaced with acidic residues (glutamic acid, or "E")) exhibits greatly diminished non-specific cytotoxicity. This mutant form of PE is sometimes referred to as PE4E.

PE40 is a truncated derivative of PE as previously described in the art. See, Pai, et al., *Proc. Nat'l Acad. Sci. USA* 88:3358–62 (1991); and Kondo, et al., *J. Biol. Chem.* 263:9470–9475 (1988). PE35 is a 35 kD carboxyl-terminal fragment of PE in which amino acid residues 1–279 have deleted and the molecule commences with a met at position 280 followed by amino acids 281–364 and 381–613 of native PE. PE35 and PE40 are disclosed, for example, in U.S. Pat. Nos. 5,602,095 and 4,892,827.

In some preferred embodiments, the cytotoxic fragment PE38 is employed. PE38 is a truncated PE pro-protein composed of amino acids 253–364 and 381–613 which is activated to its cytotoxic form upon processing within a cell (see e.g., U.S. Pat. No. 5,608,039, and Pastan et al., *Biochim. Biophys. Acta* 1333:C1–C6 (1997)).

As noted above, some or all of domain 1b may be deleted, and the remaining portions joined by a linker or directly by a peptide bond. Some of the amino portion of domain II may be deleted. And, the C-terminal end may contain the native sequence of residues 609–613 (REDLK; SEQ ID NO:8), or may contain a variation found to maintain the ability of the construct to translocate into the cytosol, such as REDL (SEQ ID NO:7) or KDEL (SEQ ID NO:6), and repeats of these sequences. See, e.g., U.S. Pat. Nos. 5,854,044; 5,821,238; and 5,602,095 and WO 99/51643. While in preferred embodiments, the PE is PE4E, PE40, or PE38, any form of PE in which non-specific cytotoxicity has been eliminated or reduced to levels in which significant toxicity to non-targeted cells does not occur can be used in the immunotoxins of the present invention so long as it remains capable of translocation and EF-2 ribosylation in a targeted cell.

A. Conservatively Modified Variants of PE

Conservatively modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

B. Assaying for Cytotoxicity of PE

*Pseudomonas* exotoxins employed in the invention can be assayed for the desired level of cytotoxicity by assays well known to those of skill in the art. Exemplary toxicity assays are described herein at, e.g., Example 2. Thus, cytotoxic fragments of PE and conservatively modified variants of such fragments can be readily assayed for cytotoxicity. A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative variants of PE.

C. Other Therapeutic Moieties

Antibodies of the present invention can also be used to target any number of different diagnostic or therapeutic compounds to cells expressing mesothelin on their surface. Thus, an antibody of the present invention, such as an anti-mesothelin scFv, may be attached directly or via a linker to a drug that is to be delivered directly to cells bearing mesothelin. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-mesothelin antibody may be an encapsulation system, such as a liposome or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735; and Connor, et al., *Pharm. Ther.* 28:341–365 (1985).

D. Detectable Labels

Antibodies of the present invention may optionally be covalently or non-covalently linked to a detectable label. Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^{3}H$, $^{125}I$, $^{35}s$, $^{14}C$, or $^{32}p$), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

E. Conjugation to the Antibody

In a non-recombinant embodiment of the invention, effector molecules, e.g., therapeutic, diagnostic, or detection moieties, are linked to the anti-mesothelin antibodies of the present invention using any number of means known to those of skill in the art. Both covalent and noncovalent attachment means may be used with anti-mesothelin antibodies of the present invention.

The procedure for attaching an effector molecule to an antibody will vary according to the chemical structure of the EM. Polypeptides typically contain a variety of functional groups; e.g., carboxylic acid (COOH), free amine (—NH$_2$) or sulfhydryl (—SH) groups, which are available for reaction with a suitable functional group on an antibody to result in the binding of the effector molecule.

Alternatively, the antibody is derivatized to expose or to attach additional reactive functional groups. The derivatization may involve attachment of any of a number of linker molecules such as those available from Pierce Chemical Company, Rockford Ill.

A "linker", as used herein, is a molecule that is used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages which are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

VII. Pharmaceutical Compositions and Administration

The antibody and/or immunoconjugate compositions of this invention (i.e., PE linked to an antibody with at least 5 times the affinity for an antigen as its parental antibody, along with antibody E4), are particularly useful for parenteral administration, such as intravenous administration or administration into a body cavity or lumen of an organ. For example, ovarian malignancies may be treated by intravenous administration or by localized delivery to the tissue surrounding the tumor. To treat mesotheliomas, pharmaceutical compositions of this invention comprising anti-mesothelin antibodies can be administered directly into the pleural or peritoneal cavities.

The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical immunotoxin composition of the present invention for intravenous administration would be about 0.1 to 10 mg per patient per day. Dosages from 0.1 up to about 100 mg per patient per day may be used, particularly if the drug is administered to a secluded site and not into the circulatory or lymph system, such as into a body cavity or into a lumen of an organ. Actual methods for preparing administrable compositions will be known or apparent to those skilled in the art and are described in more detail in such publications as REMINGTON'S PHARMACEUTCAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219–342 (1994); and Tice & Tabibi, TREATISE ON CONTROLLED DRUG DELIVERY, A. Kydonieus, ed., Marcel Dekker, Inc. New York, N.Y., pp. 315–339, (1992) both of which are incorporated herein by reference.

Polymers can be used for ion-controlled release of immunoconjugate compositions of the present invention. Various degradable and nondegradable polymeric matrices for use in controlled drug delivery are known in the art (Langer, R., *Accounts Chem. Res.* 26:537–542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., *Pharm. Res.* 9:425–434 (1992); and Pec, et al., *J. Parent. Sci. Tech.* 44(2):58–65 (1990)). Alternatively, hydroxyapatite has been used as a microcarrier for controlled release of proteins (Ijntema, et al., *Int. J. Pharm.* 112:215–224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the immunotoxins of the present invention are included a variety of disease conditions caused by specific human cells that may be eliminated by the toxic action of the fusion protein. One preferred application for the immunotoxins of the invention is the treatment of malignant cells expressing mesothelin. Exemplary malignant cells include ovarian, stomach and squamous cell cancers as well as mesotheliomas.

VIII. Diagnostic Kits and In vitro Uses

In another embodiment, this invention provides for kits for the detection of mesothelin or an immunoreactive fragment thereof, (i.e., collectively, a "mesothelin protein") in a biological sample. A "biological sample" as used herein is a sample of biological tissue or fluid that contains mesothelin. Such samples include, but are not limited to, tissue from biopsy, sputum, amniotic fluid, blood, and blood cells (e.g., white cells). Fluid samples may be of some interest, but are generally not preferred herein since detectable concentrations of mesothelin are rarely found in such a sample. Biological samples also include sections of tissues, such as frozen sections taken for histological purposes. A biological sample is typically obtained from a multicellular eukaryote, preferably a mammal such as rat, mouse, cow, dog, guinea pig, or rabbit, and more preferably a primate, such as a macaque, chimpanzee, or human.

Kits will typically comprise an anti-mesothelin antibody of the present invention. In some embodiments, the anti-mesothelin antibody will be an anti-mesothelin Fv fragment, such as a scFv fragment. The kits can include an E4 antibody.

In addition the kits will typically include instructional materials disclosing means of use of an antibody of the present invention (e.g. for detection of mesothelial cells in a sample). The kits may also include additional components to facilitate the particular application for which the kit is designed. Thus, for example, the kit may additionally contain means of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

In one embodiment of the present invention, the diagnostic kit comprises an immunoassay. As described above, although the details of the immunoassays of the present invention may vary with the particular format employed, the method of detecting mesothelin in a biological sample generally comprises the steps of contacting the biological sample with an antibody which specifically reacts, under immunologically reactive conditions, to mesothelin. The antibody is allowed to bind to mesothelin under immunologically reactive conditions, and the presence of the bound antibody is detected directly or indirectly.

Due to the increased affinity of antibodies developed by the methods taught herein, and of the antibodies designated SS1, D8, and C10, in particular, the antibodies provided herein will be especially useful as diagnostic agents and in in vitro assays to detect the presence of mesothelin in biological samples. For example, the antibodies SS1, D8, C10, and other antibodies made by the methods taught herein can be used as the targeting moieties of immunoconjugates in immunohistochemical assays to determine whether a sample contains cells expressing mesothelin. If the sample is one taken from a tissue of a patient which should not normally express mesothelin, detection of mesothelin would indicate either that the patient has a cancer characterized by the presence of mesothelin-expressing cells, or that a treatment for such a cancer has not yet been successful at eradicating the cancer. The antibody E4 can also be used for these purposes.

In another set of uses for the invention, immunotoxins targeted by antibodies of the invention can be used to purge targeted cells from a population of cells in a culture. Thus, for example, cells cultured from a patient having a cancer expressing mesothelin can be purged of cancer cells by contacting the culture with immunotoxins which use SS1, D8, or C10 scFvs as a targeting moiety. The E4 scFv can also be used as a targeting moiety for these purposes.

Although the present invention has been described in some detail by way of illustration and example for purposes of clarity of understanding, it will be obvious that certain changes and modifications may be practiced within the scope of the appended claims.

IX. Examples

EXAMPLE 1

Construction of the Libraries

Of the 32 hotspots in SS(scFv), 14 are located in the VH and 18 in the VL. We chose the CDR3s to begin mutagenesis because they are the major sites of interaction with the antigen. We chose VL CDR3 over VH CDR3 for our initial studies because it undergoes fewer recombination events and is therefore closer to the germline. In the CDR3 of VL there are two hotspots of the A/G-G-C/T-A/T type and one AGT serine codon. We began our experiments by concentrating on the tetranucleotide hotspots in VL CDR3. In our study we randomized all the nucleotides of the codons that form whole or part of the tetranucleotide motif unless there was a special reason not to do so (discussed below).

The first phage library (Lib 89/93/94) involved randomizations of codons which are part of two tetranucleotide hotspots, one encoding residues 89 and 90 and the other residues 93 and 94 in the VL. Because Q90 is highly conserved in sub group VI (Johnson et al., in *WEIR'S HANDBOOK OF EXPERIMENTAL IMMUNOLOGY I. IMMUNOCHEMISTRY AND MOLECULAR IMMUNOLOGY*, 5$^{th}$ Ed., Herzenberg et al. eds., Blackwell Science Inc., Cambridge, Mass., Chapter 6, pp. 6.1–6.21 (1996)) to which SS VL belongs, we chose to leave it unchanged and randomized residues 89, 93 and 94. A library in which three amino acids are randomized should have $8 \times 10^3$ different protein variants and in terms of all different nucleotide combinations (using NNS oligos) the complete repertoire would contain $3 \times 10^4$ different clones. The library we made contained $6 \times 10^4$ clones and is expected to cover virtually all the possibilities.

After panning and analysing Lib 89/93/94 we found that Q89 was conserved in all the binders but substitutions were tolerated at positions 93 and 94. Using this information we constructed a second library, Lib 92–94, in which the AGT codon (another type of hotspot) for S92 was mutated along with the codons for G93 and Y94. The size of this library was $1 \times 10^5$.

As controls for our experiments we made two libraries (Lib 89–91 and Lib 95–97). Lib 89–91 was made to examine the effect of randomizing conserved residues within a hotspot and Lib 95–97 was made to study effects of randomizing residues outside the hotspots. In these libraries, three codons were randomized to allow comparison with the other two libraries in which three codons located in rationally selected hotspots were randomized. The size of each of these libraries was also $1 \times 10^5$.

EXAMPLE 2

Panning of the Libraries and Enrichment of Binders

The libraries were panned on immobilized recombinant mesothelin. The results of the panning experiments are shown in Table 3. We know that with an input of $2-6 \times 10^{11}$ phage the background is usually around $5-6 \times 10^4$. For Lib 89/93/94 and Lib 92–94 we obtained $2 \times 10^5$ phage from the first panning. This represents an enrichment of about 3-fold of phages that bind mesothelin. At the second round, there was a large increase in enrichment which was 150 and 130-fold, respectively. The enrichment after the third round of panning for these libraries were about 5-fold. The overall enrichment was about 2000. In contrast, for the control libraries there was no enrichment after the first round of panning but thereafter there was a gradual increase in enrichment, 10-fold after second panning and 200-fold after the third. The overall enrichment for both the control libraries was also about 2000-fold. Although the overall enrichment for all the libraries were similar, the pattern of enrichment was strikingly different. The early and rapid enrichment of two libraries, Lib 89/93/94 and Lib 92–94 indicates that both contained a large number of binders. In contrast the slow and gradual enrichment of the control libraries, Lib 89–91 and Lib 95–97 suggests that they contained fewer binders which were slowly enriched during successive rounds of panning.

TABLE 3

Enrichment of mesothelin binding phage from the libraries by panning on recombinant mesothelin.
*Refers to enrichment over the background level of phage binding which is $5-6 \times 10^4$ for an input phage number of $2-6 \times 10^{11}$

| Panning of | Panning Round | Input number of phage | Recovered number of phage | Enrichment over previous round | Total Enrichment |
|---|---|---|---|---|---|
| Lib 89/93/94 | 1 | $3 \times 10^{11}$ | $2 \times 10^5$ | 3* | |
| | 2 | $3 \times 10^{11}$ | $3 \times 10^7$ | 150 | |
| | 3 | $10^{11}$ | $5 \times 10^7$ | 5 | 2250 |
| Lib 92–94 | 1 | $2.6 \times 10^{11}$ | $2.1 \times 10^5$ | 3* | |
| | 2 | $2.8 \times 10^{11}$ | $3 \times 10^7$ | 132 | |
| | 3 | $2 \times 10^{11}$ | $9 \times 10^7$ | 5 | 1980 |
| Lib 89–91 | 1 | $6.75 \times 10^{11}$ | $5.6 \times 10^4$ | 0 | |
| | 2 | $4.1 \times 10^{11}$ | $3.8 \times 10^5$ | 10 | |
| | 3 | $3 \times 10^{11}$ | $5.3 \times 10^7$ | 200 | 2000 |
| Lib 95–97 | 1 | $2 \times 10^{11}$ | $6 \times 10^4$ | 0 | |
| | 2 | $2 \times 10^{11}$ | $8 \times 10^5$ | 10 | |
| | 3 | $10^{11}$ | $7.9 \times 10^7$ | 198 | 1980 |

EXAMPLE 3

Screening of Clones for Mesothelin Binding

Figure 2:
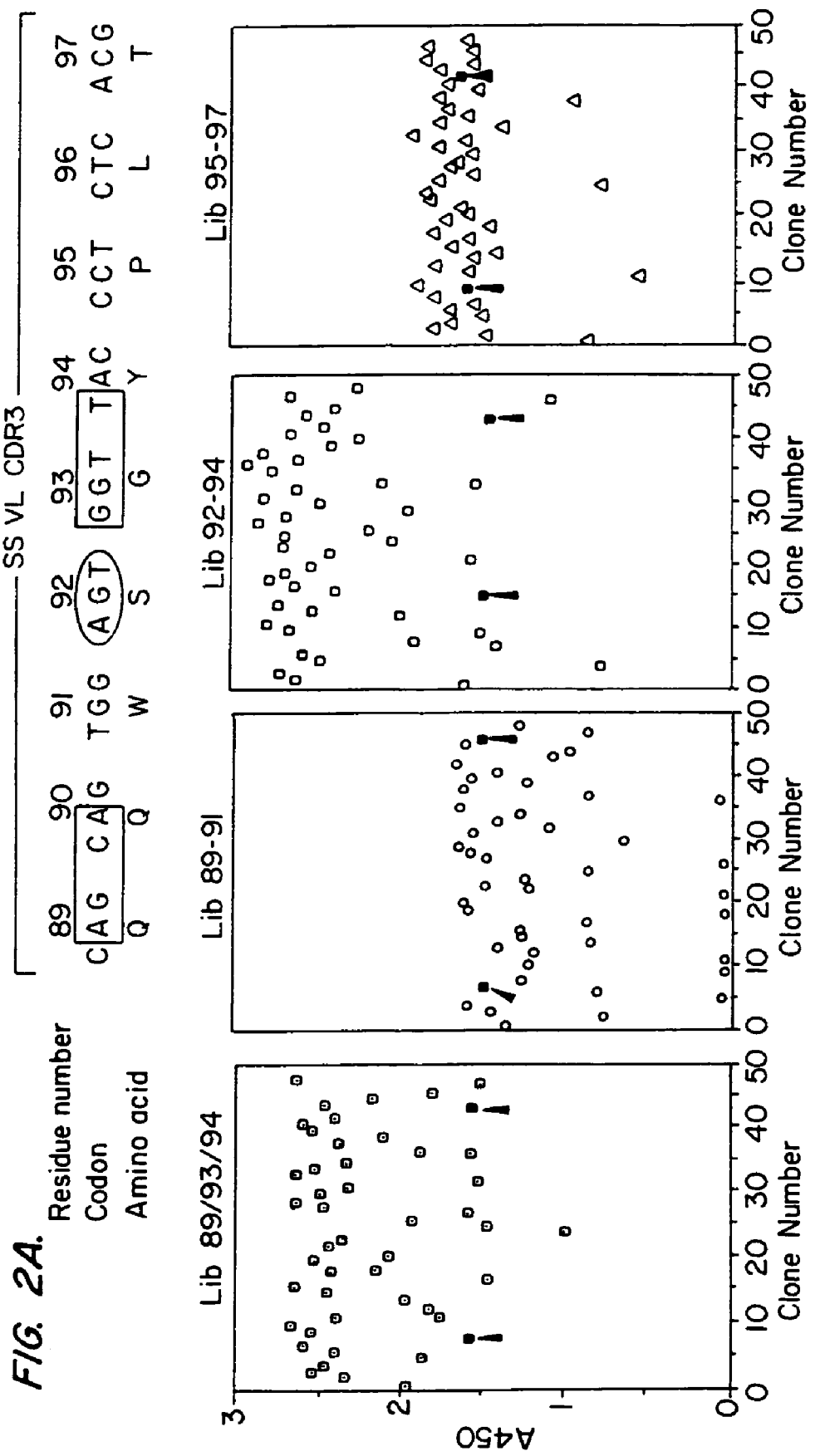
FIG. 2: Mesothelin binding as judged by ELISA of phage clones selected after panning each of the four libraries.

Next, we examined the binding properties of phage selected from each of the different libraries. For each library we screened 23 clones by ELISA from the second and third rounds of the panning. The results of this experiment are shown in FIG. 2.

FIG. 2B shows the mesothelin binding activity of clones selected after panning of Lib 89/93/94. As evident from the figure, all 46 clones bound to mesothelin and could be grouped into 4 types: (i) 27 clones had very high ELISA signals (2.3–2.7); (ii) 12 clones with high ELISA signals (1.75–2.2); (iii) 6 clones had ELISA signals comparable to the parental SS(scFv) phage (shown by filled squares) and (iv) one clone had an ELISA signal lower than the wild type parental phage.

FIG. 2C shows the mesothelin binding activity of phage clones from the Lib 89–91. Of the 46 clones tested, 39 bound mesothelin. None had an ELISA signal greater than the parental clone. 28 of these 39 clones had ELISA signals similar to the parental clone (1.25 to 1.5). The remaining 11 clones had ELISA signals lower than the parental type.

FIG. 2D shows the mesothelin binding activity of phage clones selected from Lib 92–94. Like those from Lib 89/93/94 library, all the 46 clones tested bound mesothelin and could be categorized into the following 4 groups. (i) 31 gave very high ELISA signal (2.3–2.9); (ii) 8 clones had a high ELISA signal (1.8–2.2); (iii) 5 clones gave ELISA signal similar to the parental type; and (iv) 2 clones had ELISA signal lower than that of the parental type.

FIG. 2E shows the mesothelin binding activity of clones selected after panning of Lib 95–97. All 46 clones tested were found to bind mesothelin and could be arranged into three groups based on ELISA signals. (i) 22 gave ELISA signal slightly better than the parental type; (ii) 20 clones had ELISA signal similar to the wild type; and (iii) 4 clones had ELISA signals below the parental type.

Twelve phage preps from each library were titrated and their numbers as determined by CFUs (colony forming units) were found to vary by less than 2-fold, indicating differences in ELISA signals were not due to differences in the number of input phage (data not shown). Also no binding to BSA was detected for phage particles from any of the clones (data not shown). These results indicate that: (i) the screening assay employed was dependable for identifying clones which made phage with better binding to mesothelin, and (ii) targeting random mutations to rationally selected hotspots leads to isolation of better binders more easily than by randomly mutating every codon of the CDRs.

EXAMPLE 4

Diversity of Clones

Twenty-four ELISA positive clones were sequenced from each library. The results are shown in FIG. 3.

From the library, Lib 89/93/94, 4 different sequences were obtained. All the clones had preserved the parental residue, glutamine, at position 89. The residues at position 93 and 94 varied. The most abundant clone had G93K-Y94H mutations. It is also the clone which had the highest ELISA signal, and was named SS 1.

From Lib 89–91, all the 24 clones sequenced had ELISA signals similar to wild type SS(scFv) and all 24 had wild type residues.

From Lib 92–94, 7 different amino acid sequences were obtained (FIG. 3). The most abundant clones were D8 (S92G-G93F-Y94N) and C10 (S92G-G93S-Y94H). From this library we obtained 2 clones (E9 and E2) with identical amino acid sequence to SS1 and D7 from Lib 89/93/94. D8, C10 and SS1 are the clones which had the highest ELISA signals.

From the library Lib 95–97, 24 clones with ELISA signals similar or greater than SS(scFv) were sequenced. Seventeen clones had the L96T mutation. The other 7 clones had the wild type amino acids. We call the L96T mutant E4(scFv).

In every case, the entire scFv coding region was sequenced to ensure that no other mutations had occurred. In terms of protein sequence 10 different types of mutants were obtained. Many of these were encoded by several different nucleotide sequences. 9 of these 10 mutants were obtained from libraries in which mutations were targeted to rationally selected hotspots (Lib 89/93/94 and Lib 92–94). Thus the presence of several clones with binding activity from these libraries agrees with the rapid enrichment pattern seen for these libraries. In contrast, Lib 89–91 which has conserved residues in hotspots, failed to yield any binder other than the parental clone, and Lib 95–97 in which mutations were targeted to non-hotspot regions, yielded a single variant. The rarity of binders in these libraries also agree with their slow and gradual enrichment pattern.

EXAMPLE 5

Construction and Purification of Immunotoxins

In immunotoxins, scFvs directed against a cancer cell surface antigen are fused in frame with a toxin, such as a truncated mutant of *Pseudomonas* exotoxin A. The antigen binding properties of the immunotoxins are determined by the scFv while the toxic moiety serves an effector function which kills the cell to which the scFv binds. Therefore, by making and purifying immunotoxins containing the mutant Fvs, we can determine the antigen binding kinetics of the scFv and also study its cytotoxic activity in cell culture. Based on a more detailed ELISA with purified phage preparations of the different clones (results not shown) we selected four scFvs to construct and purify immunotoxins. Among these four, SS1, D8 and C10 represent the best clones obtained from libraries in which rationally selected hotspots were randomized, and E4 represents the only clone which had better binding than the parental SS(scFv) obtained from control libraries. The immunotoxins were purified to over 95% homogeneity and eluted as a monomer in TSK gel filtration chromatography (result not shown). These purified immunotoxins were used to determine the affinities of the scFvs and also to study their cell killing activities.

EXAMPLE 6

Binding Characteristics of the Immunotoxins

Figure 4:
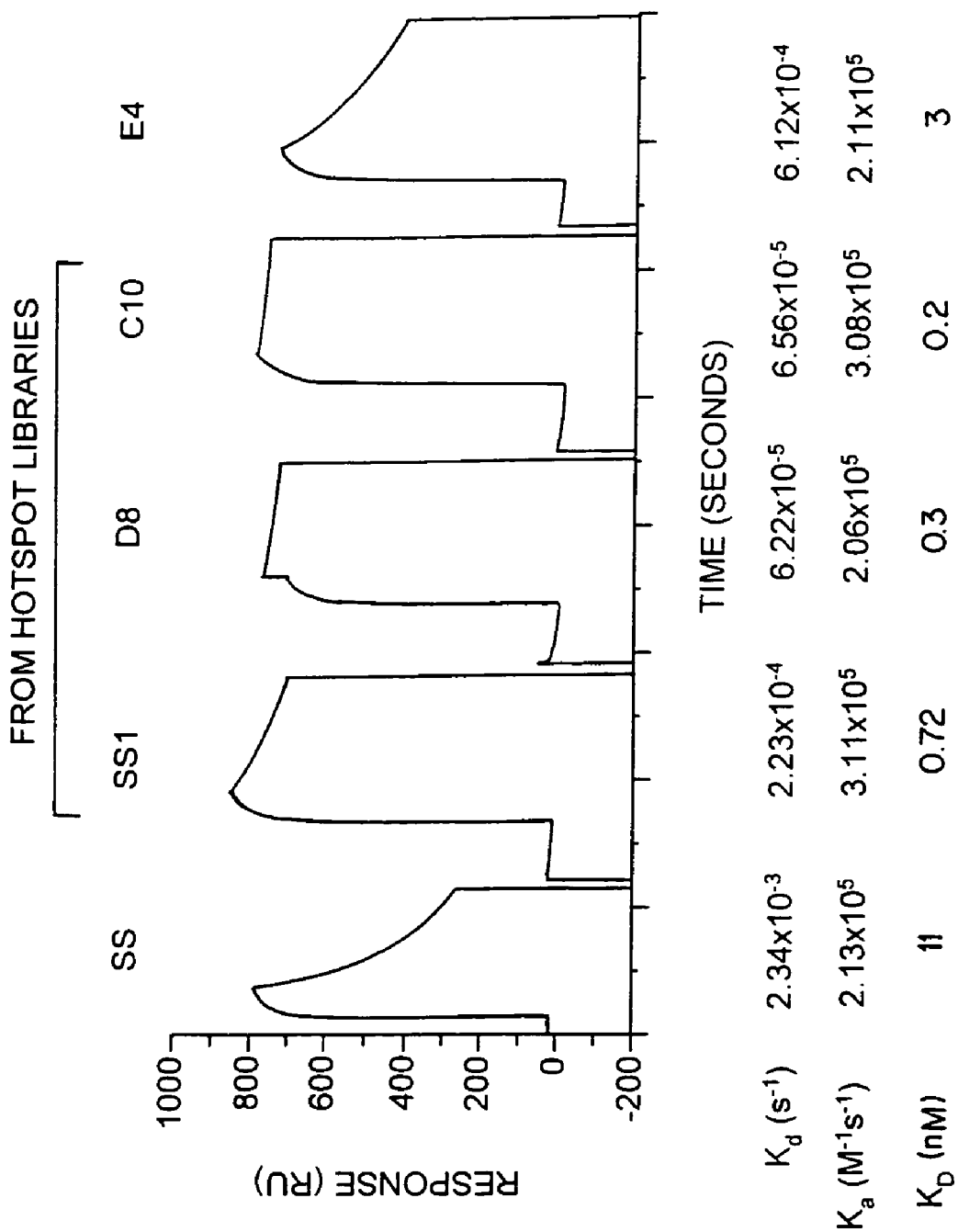
FIG. 4: Comparison of the BIAcore sensorgrams obtained for the binding of wild type and mutated scFv immunotoxins to immobilized mesothelin. From left to right the targeting moiety of the immunotoxins are: the parental SS, and the mutated variants SS1, D8, C10 and E4. The values for $K_{offs}$, $K_{ons}$ and $K_{Ds}$ are tabulated below the Figure. "RU" stands for "resonance units." The X-axis represents time in seconds.

The binding characteristics of the scFvs selected by panning the phage libraries were determined using the corresponding purified immunotoxins for surface plasmon resonance (BIAcore) studies. FIG. 4 shows representative sensorgrams of the binding of immunotoxins to mesothelin and lists the values for the kons, koffs and KDs. It is apparent that all the mutants (SS1, D8, C 10 and E4) had better binding to mesothelin than the parental SS(scFv)-PE38. The on rates of SS1 and C 10 were about 1.5-fold higher while those of D8 and E4 were about the same as the parental SS(scFv). The off rates of SS1, D8, C10 and E4 were decreased by 10, 37, 35 and 3.8-fold, respectively, compared to the parental SS(scFv). Similar to what others have reported, the increased binding of the mutants observed in the present study was due mainly to a decrease in their off rates (Schier et al., *J. Mol. Biol.* 255: 28–43 (1996); Yelton et al., *J. Immunol.*, 155:1994–2004 (1995); Yang et al., *J. Mol. Biol.* 254:392–403 (1995)). These data show that SS1, D8 and C10 which are derived from libraries in which rationally selected hotspots were mutated showed a 15, 37 and 55-fold increase in affinity, respectively, over the parental Fv, whereas E4 which is the only mutant isolated from control libraries showed a more modest 3.7-fold increase in affinity over the parental SS(scFv).

EXAMPLE 7

Cytotoxic Activity of the Immunotoxins

For evaluating the usefulness of the higher affinity scFvs as targeting agents in cancer therapy, we determined the cytotoxicity of the immunotoxins made with the different scFvs. Table 4 shows the cytotoxic activity of the various immunotoxins on antigen positive A1847 and antigen negative HUT 102 cell lines. On A1847 cells, SS1, D8 and C10 scFv-PE38 were over 10-fold more active than the wild-type SS(scFv) immunotoxin, while E4(scFv)-PE38 was only about 2-fold more active. Cytotoxicity on HUT 102 (antigen negative cells) was not evident. Thus the increase in affinity obtained by targeting mutations to rationally selected hotspots resulted in a large increase in cytotoxic activity. The increase in cytotoxicity, however, was not proportionally related to the increase in affinity. For example, the $IC_{50}$s of SS1(Fv)-PE38 and C10(Fv)-PE38 were very similar, whereas, their affinities differed by about three-fold (the $IC_{50}$ is the amount of immunotoxin required to inhibit protein synthesis by 50%). This difference could be due to the fact that the affinities were measured using recombinant protein made in E. coli, whereas the cytotoxicity was measured on an ovarian cancer cell line expressing the antigen.

This strategy has been applied in our laboratory to another antibody that binds to a mutant form of epidermal growth factor receptor. It has been possible to isolate mutants with higher affinities in this study also (Beers, R., Chowdhury, P. S. and Pastan, I. manuscript in preparation). We have also mutated the CDR3 heavy chain of SS. ELISA studies of these mutants show affinity to mesothelin higher than that of the parental SS scFv. These results strongly indicate that it should be easier to select better binding phage from small libraries made by targeting mutations to rationally selected hotspots than by the currently used methods.

In the present work we selected four positions for randomization (three within and one outside of a hotspot) and the modified mutants have been found to be useful. The improvements obtained by our approach is comparable to those attained from the large phage libraries described in the literature (Schier et al., J. Mol. Biol. 255: 28–43 (1996); Yelton et al., J. Immunol., 155:1994–2004 (1995); Yang et al., J. Mol. Biol. 254:392–403 (1995); Pini et al., J. Biol. Chem. 273:21769–21776 (1998); Wu et al., Proc. Natl. Acad. Sci. USA 95:6037–6042 (1998)). We suggest that by mimicking the natural somatic hypermutation process, one can readily obtain recombinant antibodies with increased affinity for antigen either from immunized or non-immunized libraries.

TABLE 4

Cytotoxicity of immunotoxins made with the parental and mutated scFvs on human ovarian adenocarcinoma cell line A1847 and T-cell leukemia line HUT102. For comparison the $K_D$ values obtained by BIAcore analysis and the relative increase in affinity of the mutants over the wild type immunotoxin are included.

|  | A1847 | $IC_{50}$ (ng/ml) on HUT 102 | Relative increase in cytotoxicity | $K_D$ | Relative increase in affinity |
|---|---|---|---|---|---|
| SS | 16 | >1000 | 1 | 1 | 1 |
| SS1 | 1.2 | >1000 | 13 | 0.72 | 15 |
| D8 | 1.4 | >1000 | 11 | 0.3 | 37 |
| C10 | 1.4 | >1000 | 11 | 0.2 | 55 |
| E4 | 8 | >1000 | 2 | 3 | 4 |

EXAMPLE 8

Construction of Libraries

Phagemid pPSC 7-1 is a phage antibody display vector coding for the mesothelin binding SS(scFv) (Chowdhury 1998). Analysis of the nucleotide sequence of SS(scFv) revealed 32 hot-spots. Of these 32 hotspots three were selected for targeting mutations. These are located in the CDR3 of the VL encoding residues 89, 90, 92, 93 and 94. Single stranded uracil containing DNA of pPSC 7-1 was prepared as described earlier (Chowdhury et al. J. Mol. Biol. 281:917–928 (1998)). A stop codon and a diagnostic Hpa1 restriction site was introduced into the CDR3 of the VL by Kunkel's mutagenesis (Kunkel, T. A., Proc. Natl. Acad. Sci. USA 82:488–492 (1985)) to produce the phagemid pPSC 7-1-94. The stop codon was introduced to prevent over representation of the wild-type sequence in the library since this mutagenesis approach gives a background of 10–12%. Uracil containing ssDNA of pPSC 7-1-94 was used as a template to construct two experimental and two control libraries using degenerate oligos. Oligo SS VL 89/93/94 5'GCACCGAACGTGAGAGG SNNSNNACTCCACTGSNNGCAGTAATAAGTTGC 3' (SEQ ID NO:9) was used for making the library Lib 89/93/94. This oligo randomizes codons 89, 93 and 94 of the VL in SS(scFv) with all twenty different amino acids. As with all the other libraries described below, this oligo replaces the stop codon at position 94 with that of a tyrosine and does not create ocher and opal stop codons.

The second library, Lib 92–94 was made using oligo SS VL Mut 92–94, 5' GCACCGAACGTGAG AGGSNNSNNSNNCCACTGCTGGCAGTAATAAG 3' (SEQ ID NO: 10) which randomizes residues 92–94. Residues 92–94 are encoded by two different hotspots placed side by side. The third and fourth libraries were made as controls. The third library, Lib 89–91, was made with the oligo SS VL Mut 89–91, 5'GCACCGAACGTGAGAGGG-TAACCACTSNNSNNS NNGCAGTAATAAGTTGC (SEQ ID NO:11) 3' which randomizes residues 89–91. Residue 90 is a conserved residue in a hotspot. Residue 91 falls outside of the hotspot. The fourth library Lib 95–97 was made with the oligo SS VL Mut 95–975'CTTTGTCCCAGCACC GAASNNSNNSNNGTAACCACTCCACTGCTGCG 3' (SEQ ID NO:12). It randomizes residues 95–97 all of which fall outside the hotspots.

EXAMPLE 9

Panning of the Libraries and Analysis of Selected Phage Clones

Panning of the libraries was done as described earlier (Chowdhury 1998). For each library 23 clones after the second and 23 clones after the third round of panning were analyzed by ELISA for mesothelin binding as follows. Single colonies were inoculated into 125 μl of 2XYT medium containing 100 μg/ml ampicillin and 2% glucose present in 96 wells of a microtiter plate. The plates were incubated at 37° C./200 rpm in a humidified incubator for 3.5 hours. 25 μl of culture from each well of these plates (master plates) were transferred to corresponding wells of another microtiter plate containing 125 μl of 2XYT medium with 100 μg/ml ampicillin, 2% glucose and about $4 \times 10^9$ pfu/ml of M13KO7. This plate (phage plate) was then incubated for 2 hours under the same conditions as described above. The phage plate was then centrifuged at 2000 rpm for 5 minutes at room temperature. The supernatant from each well was removed by gently shaking the plate in an inverted position. The cell pellet in each well was resuspended in 200 μl of 2XYT medium containing 100 μl/ml ampicillin, and 50 μg/ml kanamycin. The plate was then incubated over night as described above. After 14–16 hours the phage plate was

EXAMPLE 10

Construction of Plasmids for Expression and Purifications of Immunotoxins

Phagemids pPSC7-1-1,7-1-2,7-1-3 and 7-1-4 code, respectively, for SS(scFv) with the following mutations in the VL: G93K-Y94H, S92G-G93F-Y94N, S92G-G93S-Y94H and L96T. The scFvs from these phagemid vectors were PCR amplified using primer pairs New G2 Nde I and New G2 Hind III (Chowdhury 1998). After purification, the PCR products were cloned into an E. coli expression vector as described before (Brinkmann et al., Proc. Natl. Acad. Sci. USA 88: 8616–8620 (1991)). The resulting plasmids, pPSC 7-2-1, pPSC 7-2-2, pPSC 7-2-3 and pPSC 7-2-4 had the scFvs fused in frame with a 38 kDa fragment of *Pseudomonas* exotoxin (PE) containing domains II and III. Recombinant proteins were produced from inclusion bodies as described before (Brinkmann et al., Proc. Natl. Acad. Sci. USA 88: 8616–8620 (1991)).

EXAMPLE 11

Surface Plasmon Resonance Assay

The affinity of the scFvs was determined by studying the binding kinetics of the purified immunotoxins to mesothelin by the surface plasmon resonance (BIAcore) technique. In separate experiments, different amounts (200–1000 RUs) of recombinant mesothelin were immobilized onto a BIAcore sensor chip, CM5. Then, each of the immunotoxins was passed over the immobilized mesothelin at a concentration of 380 nM. $k_{on}$ was determined from a plot of (ln (dR/dt)/t versus concentration, where R is response and t is time. $k_{off}$ was calculated during the first 1–2 minutes of the dissociation phase of the sensorgrams. These association and dissociation rates were measured under a continuous flow rate of 10 μl/min. KD was calculated by dividing $k_{off}$ by $k_{on}$.

EXAMPLE 12

Cytotoxicity Assays

Cytotoxic activity of the immunotoxins was determined as described before (Chaudhary et al., Nature 339:394–397 (1989)) by inhibition of protein synthesis in mesothelin positive human ovarian carcinoma line A1847 and mesothelin negative T-cell leukemia line HUT 102. The $IC_{50}$ is the amount of immunotoxin required to inhibit protein synthesis by 50%.

All publications and patents mentioned in this specification are herein incorporated by reference into the specification to the same extent as if each individual publication or patent was specifically and individually indicated to be incorporated herein by reference.

---

What is claimed is:

1. An isolated anti-mesothelin antibody comprising a variable heavy ("$V_H$") chain and a variable light ("$V_L$") chain, which $V_H$ and $V_L$ chains each have a first, a second and a third complementarity-determining region ("CDR"), wherein the first CDR ("CDR1"), the second CDR ("CDR2"), and third CDR ("CDR3"), respectively, of said heavy chain have the amino acid residue sequence shown for CDR1, CDR2, and CDR3, respectively, of the heavy chain shown in FIG. 1, and wherein CDRs 1, 2 and 3 respectively, of said $V_L$ chain, have the amino acid residue sequence shown for CDR1, CDR2, and CDR3 respectively, of the light chain shown in FIG. 1, provided that the sequence of amino acid residues in CDR3 of the $V_L$ chain differs from that shown in FIG. 1 by a substitution selected from G93K-Y94H (antibody SS1), S92G-G93F-Y94(antibody D8), S92G-G93S-Y94H (antibody C10), Y94H (antibody C5), G93A-Y94H (antibody D7), G93Q-Y94I (antibody B7), S92G-G93T-Y94N (antibody D9), S92G-G93D-Y94F (antibody C3), S92G-G93D-Y94H (antibody C4) and L96T, (antibody E4), said amino acid residues being numbered as in FIG. 3.

2. An isolated anti-mesothelin antibody of claim 1, wherein said antibody is a scFv, dsFv, a Fab, or a F(ab')$_2$.

3. An isolated anti-mesothelin antibody of claim 1, further comprising an amino acid substitution of at least one amino acid in a CDR selected from the group consisting of $V_L$ CDR1, $V_L$ CDR2, $V_H$ CDR1, and $V_H$ CDR2, said amino acid being encoded by a codon that comprises a nucleotide belonging to a hot spot motif selected from AGY or RGYW, where R is A or G, Y is C or T and W is A or T.

4. A chimeric molecule comprising a isolated anti-mesothelin antibody of claim 1 and a therapeutic moiety or a detectable label.

5. A chimeric molecule of claim 4, wherein the therapeutic moiety is a toxic moiety.

6. A chimeric molecule of claim 5, wherein the toxic moiety is a *Pseudomonas* exotoxin A ("PE").

7. A chimeric molecule of claim 6, wherein the PE is selected from the group consisting of PE35, PE38, and PE40.

8. A chimeric molecule of claim 4, wherein said antibody further comprises an amino acid substitution of at least one amino acid in a CDR selected from the group consisting of $V_L$ CDR1, $V_L$ CDR2, $V_H$ CDR1, and $V_H$ CDR2, said amino acid being encoded by a codon that comprises a nucleotide belonging to a hot spot motif selected from AGY or RGYW, wherein R is A or G, Y is C or T and W is A or T.

9. A composition comprising (a) a chimeric molecule of claim 4 and, (b) a pharmaceutically acceptable carrier.

10. A method of killing a malignant cell bearing mesothelin antigen, said method comprising contacting the cell with a chimeric molecule comprising a toxic moiety and a targeting moiety, wherein the targeting moiety has a variable heavy ("$V_H$") chain and a variable light ("$V_L$") chain which $V_H$ and $V_L$ chains each have a first complementarity determining region ("CDR"), a second CDR and a third ("CDR"), respectively, wherein the first CDR ("CDR1"), the second CDR ("CDR2"), and third CDR ("CDR3"), respectively, of said heavy chain have the amino acid residue sequence shown for CDR1, CDR2, and CDR3, respectively, of the heavy chain shown in FIG. 1, and wherein CDRs 1, 2 and 3 respectively, of said $V_L$ chain, have the amino acid residue sequence shown for CDR1, CDR2, and CDR3, respectively, of the light chain shown in FIG. 1, provided that the sequence of amino acid residues in CDR3 of the $V_L$ chain differs from that shown in FIG. 1 by a substitution selected from G93K-Y94H (antibody SS1), S92G-G93F-Y94N (antibody D8), S92G-G93S-Y94H (antibody C10), Y94H (antibody C5), G93A-Y94H (antibody D7), G93Q-Y94I (antibody B7), S92G-G93T-Y94N (antibody D9), S92G-G93O-Y94F (antibody C3), S92G-G93D-Y94H (antibody C4) and L96T (antibody E4), said amino acid residues being numbered as in FIG. 3.

11. A method of claim 10, wherein said toxic moiety is a *Pseudomonas* exotoxin A ("PE").

12. A method of claim 11, wherein the PE is selected from the group consisting of PE35, PE38, and PE40.

13. A method of claim 10, wherein said targets moiety further comprises an amino acid substitution of at least one amino acid in a CDR selected from the group consisting of $V_L$ CDR1, $V_L$ CDR2, $V_H$ CDR1, and $V_H$ CDR2, said amino acid being encoded by a codon that comprises a nucleotide belonging to a hot spot motif selected from AGY or RGYW, wherein R is A or G, Y is C or T and W is A or T.

14. An isolated nucleic acid molecule encoding an anti-mesothelin antibody comprising a variable heavy ("$V_H$") chain and a variable light ("$V_L$") chain, which $V_H$ and $V_L$ chains each have a first, a second and a third complementarity-determining region ("CDR"), wherein the first CDR ("CDR1"), second CDR ("CDR2") and third CDR ("CDR3"), respectively, of said heavy chain have the amino acid residue sequence shown for CDR1, CDR2, and CDR3, respectively, of the heavy chain shown in FIG. 1, and wherein the first CDR ("CDR1"), second CDR ("CDR2") and third CDR ("CDR3"), respectively, of said $V_L$ chain, have the amino acid residue sequence shown for CDR1, CDR2, and CDR3, respectively, of the light chain shown in FIG. 1, provided that the sequence of amino acid residues in the third CDR of the $V_L$ chain differs from that shown in FIG. 1 by a substitution selected from G93K-Y94H (antibody SS1), S92G-G93F-Y94N (antibody D8), S92G-G93S-Y94H (antibody C10), Y94H (antibody C5), G93A-Y94H (antibody D7), G93Q-Y94I (antibody B7), S92G-G93T-Y94N (antibody D9), S92G-G93D-Y94F (antibody C3), S92G-G93D-Y94H (antibody C4) and L96T (antibody E4), said amino acid residues being numbered as in FIG. 3.

15. A nucleic acid of claim 14, wherein said antibody further comprises an amino acid substitution of at least one amino acid in a CDR selected from the group consisting of the $V_L$ CDR1, the $V_L$, CDR2, the $V_H$ CDR1, and the $V_H$ CDR2, said amino acid being encoded by a codon that comprises a nucleotide belonging to a hot spot motif selected from AGY or RGYW, wherein R is A or G, Y is C or T and W is A or T.

16. An expression cassette comprising an isolated nucleic acid of claim 14 operably linked to a promoter.

17. An expression cassette of claim 16, further wherein antibody further comprises an amino acid substitution of at least one amino acid in a CDR selected from the group consisting of the first CDR of $V_L$, the second CDR of $V_L$, the first CDR of $V_H$, and the second CDR of $V_H$, said amino acid being encoded by a codon that comprises a nucleotide belonging to a hot spot motif selected from AGY or RGYW, wherein R is A or G, Y is C or T and W is A or T.

* * * * *